United States Patent
Tanabe et al.

(10) Patent No.: US 10,582,039 B2
(45) Date of Patent: Mar. 3, 2020

(54) MOBILE ELECTRONIC DEVICE AND CONTROL METHOD

(71) Applicant: KYOCERA Corporation, Kyoto-shi, Kyoto (JP)

(72) Inventors: Shigeki Tanabe, Yokohama (JP); Hideki Morita, Yokohama (JP); Isao Masuike, Machida (JP); Shinya Saito, Kawasaki (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/506,641

(22) PCT Filed: Aug. 27, 2015

(86) PCT No.: PCT/JP2015/074288
§ 371 (c)(1),
(2) Date: Feb. 24, 2017

(87) PCT Pub. No.: WO2016/031934
PCT Pub. Date: Mar. 3, 2016

(65) Prior Publication Data
US 2017/0251098 A1    Aug. 31, 2017

(30) Foreign Application Priority Data

Aug. 27, 2014 (JP) ................... 2014-172606
Dec. 24, 2014 (JP) ................... 2014-261277

(51) Int. Cl.
*H04M 1/725* (2006.01)
*G06F 1/3231* (2019.01)
(Continued)

(52) U.S. Cl.
CPC ...... *H04M 1/72569* (2013.01); *G06F 1/3231* (2013.01); *G06F 1/3234* (2013.01);
(Continued)

(58) Field of Classification Search
CPC .......... G01J 1/4204; G01J 1/44; G01B 21/16; G06F 1/1626; G06F 1/1684; G06F 1/169;
(Continued)

(56) References Cited

U.S. PATENT DOCUMENTS 8,264,340 B2   9/2012  Mazzolini et al.
8,862,427 B2  10/2014  Sakuraoka
(Continued)

FOREIGN PATENT DOCUMENTS

JP   2003-37545 A    2/2003
JP   2003-345476 A  12/2003
(Continued)

OTHER PUBLICATIONS

Extended European Search Report in EP Application No. 15836774.8, dated Mar. 8, 2018, 8pp.
(Continued)

*Primary Examiner* — Yuwen Pan
*Assistant Examiner* — Paul P Tran
(74) *Attorney, Agent, or Firm* — Hauptman Ham, LLP

(57) ABSTRACT

A mobile electronic device includes a first sensor that detects a proximity to an own device, a second sensor that detects a body reaction, and a controller that determines, when the proximity to the own device is detected by the first sensor and the body reaction is detected by the second sensor, that the own device is in a storage part provided on clothes. When it is determined that the own device is in the storage part provided on the clothes, the controller determines whether the clothes correspond to upper-body clothing or lower-body clothing of a user based on rotation information of the own device.

19 Claims, 22 Drawing Sheets

(51) Int. Cl.
*G06F 1/3234* (2019.01)
*A61B 5/024* (2006.01)
*A61B 5/0205* (2006.01)
*H04M 19/04* (2006.01)
*A61B 5/11* (2006.01)

(52) U.S. Cl.
CPC ......... *H04M 19/04* (2013.01); *H04M 19/047* (2013.01); *A61B 5/024* (2013.01); *A61B 5/0205* (2013.01); *A61B 5/1118* (2013.01); *H04M 2250/12* (2013.01)

(58) Field of Classification Search
CPC ...... G06F 1/3203; G06F 1/3231; G06F 3/017; G06F 3/0304; G06F 3/0346; G06F 3/03547; G06F 3/0383; G06F 3/041; G06F 3/0416; G06F 3/04817; G06F 3/0418; G06F 3/042; G06F 3/0485; G06F 3/04883; G06F 3/011; G06F 3/0412; G06F 17/00; G06F 1/3234; H04M 1/605; H04M 1/72563; H04M 1/72566; H04M 1/72; H04M 1/72569; H04M 1/72572; H04M 19/04; H04M 19/047; H04M 2250/12; H04W 52/0216; H04W 52/0219; H04W 52/0225; H04W 52/0251; H04W 52/0254; H04W 52/0258; H04W 52/027; H04W 52/0277; H04W 52/287; H04W 52/46; H04W 72/14; A61B 5/0059; A61B 5/01; A61B 5/02055; A61B 5/0205; A61B 5/024; A61B 5/0245; A61B 5/04012; A61B 5/0488; A61B 5/0492; A61B 5/1118; A61B 5/6804; A61B 5/4266
See application file for complete search history.

(56) References Cited

U.S. PATENT DOCUMENTS

| | | | |
|---|---|---|---|
| 9,664,902 B1 | 5/2017 | Raffle et al. | |
| 9,903,753 B2* | 2/2018 | Alameh | G01J 1/0233 |
| 2002/0142792 A1* | 10/2002 | Martinez | H04M 1/663 |
| | | | 455/550.1 |
| 2003/0148760 A1 | 8/2003 | Takayanagi | |
| 2003/0197597 A1 | 10/2003 | Bahl et al. | |
| 2005/0136994 A1 | 6/2005 | Bahl et al. | |
| 2006/0019724 A1 | 1/2006 | Bahl et al. | |
| 2006/0116178 A1* | 6/2006 | Vuong | H04M 1/72566 |
| | | | 455/574 |
| 2008/0006762 A1 | 1/2008 | Fadell et al. | |
| 2010/0304757 A1 | 12/2010 | Yoshioka | |
| 2010/0306711 A1* | 12/2010 | Kahn | G06F 3/017 |
| | | | 715/863 |
| 2011/0151938 A1 | 6/2011 | Hashimoto et al. | |
| 2011/0282620 A1 | 11/2011 | Sakuraoka | |
| 2011/0319128 A1* | 12/2011 | Miwa | H04M 1/6008 |
| | | | 455/550.1 |
| 2012/0206234 A1* | 8/2012 | Case, Jr. | A41D 1/002 |
| | | | 340/5.8 |
| 2013/0119255 A1 | 5/2013 | Dickinson et al. | |
| 2013/0130725 A1* | 5/2013 | Forutanpour | G01C 21/165 |
| | | | 455/456.6 |
| 2013/0150006 A1* | 6/2013 | Nunally | H04W 4/21 |
| | | | 455/414.1 |
| 2013/0194066 A1* | 8/2013 | Rahman | G05B 1/01 |
| | | | 340/5.51 |
| 2013/0222243 A1 | 8/2013 | Jung et al. | |
| 2014/0018097 A1* | 1/2014 | Goldstein | G06F 19/00 |
| | | | 455/456.1 |
| 2014/0120990 A1* | 5/2014 | Parco | H04W 52/0229 |
| | | | 455/574 |
| 2014/0289835 A1 | 9/2014 | Varshavsky et al. | |
| 2015/0087925 A1* | 3/2015 | Pedley | A61B 5/024 |
| | | | 600/301 |

FOREIGN PATENT DOCUMENTS

| | | | |
|---|---|---|---|
| JP | 2005-136845 | A | 5/2005 |
| JP | 2009-296171 | A | 12/2009 |
| JP | 2010-62849 | A | 3/2010 |
| JP | 2010-207485 | A | 9/2010 |
| JP | 2011-257374 | A | 12/2011 |
| JP | 2013-175187 | A | 9/2013 |
| JP | 2013-255192 | A | 12/2013 |
| WO | 2009/147779 | A1 | 12/2009 |
| WO | 2010/007765 | A1 | 1/2010 |

OTHER PUBLICATIONS

Office Action in JP Application No. 2014-261277, dated Oct. 31, 2017, for which an explanation of relevance is attached. 3pp.
Hayashi Tomotaka, "Design and Implementation of a Context-Aware Content Delivery Service Using Tiny Mobile Sensors" Technical report of The Institute of Electronics, Information and Communication Engineers, Feb. 24, 2005, pp. 149-154, vol. 104, The Institute of Electronics, Information and Communication Engineers, Japan, with a partial English translation.
Office Action in JP Application No. 2014-261277, dated May 16, 2017, for which an explanation of relevance is attached.
International Search Report in PCT/JP2015/074288, dated Nov. 10, 2015.
Kurasawa et al., "User Posture and Movement Estimation Based on 3-Axis Acceleration Sensor Position on the User's Body" IPSJ SIG Notes, May 23, 2006, pp. 15 to 22, vol. 2006, No. 54, ISSN 0919-6072.
Shigenori Tanaka et al., Development of Health Management Application, Proceedings of the 76th (2014) Annual Conference of the Information Processing Society of Japan (4), IPSJ, Mar. 11, 2014, pp. 4-575 to 4-576, Japan, 8pp.
Extended European Search Report in EP Application No. 15835525. 5, dated Mar. 8, 2018, 8pp.
International Search Report in PCT/JP2015/074287, dated Nov. 10, 2015, 6pp.

* cited by examiner

MOBILE ELECTRONIC DEVICE AND CONTROL METHOD

RELATED APPLICATIONS

The present application is a National Stage of PCT International Application No. PCT/JP2015/074288, filed Aug. 27, 2015, which claims priority to Japanese Patent Application Nos. 2014-172606, filed Aug. 27, 2014 and 2014-261277, filed Dec. 24, 2014.

FIELD

The present application relates to a mobile electronic device and a control method.

BACKGROUND

Conventionally, some mobile electronic devices such as mobile phones and smartphones are those equipped with various sensors for the purpose of detecting situations where a mobile electronic device is placed.

SUMMARY

A mobile electronic device according to one of aspects of the present invention includes a first sensor that detects a proximity to its own device, a second sensor that detects a body reaction, and a controller that determines, when the proximity to the own device is detected by the first sensor and the body reaction is detected by the second sensor, that the own device is in a storage part provided on clothes.

A mobile electronic device according to one of aspects of the present invention includes a sensor configured to detect a proximity to an own device and a body reaction triggered by detection of the proximity to the own device, and a controller configured to determine, when the body reaction is detected by the sensor, that the own device is in a storage part provided on clothes.

A control method according to another aspect of the present invention is a control method executed by a mobile electronic device having a sensor. The control method includes steps of detecting a proximity to its own device, detecting a body reaction when the proximity to the own device is detected, and determining, when the body reaction is detected, that the own device is in a storage part provided on clothes.

DESCRIPTION OF EMBODIMENTS

However, there is room for improvement in the technology for detecting situations where a mobile electronic device is placed. From the above, it is necessary to provide a mobile electronic device and a control method with improved technology for detecting situations where a mobile electronic device is placed. A plurality of embodiments for implementing the mobile electronic device and the control method according to the present application will be explained in detail below with reference to the accompanying drawings. A smartphone will be explained below as an example of the mobile electronic device.

Figure 1:
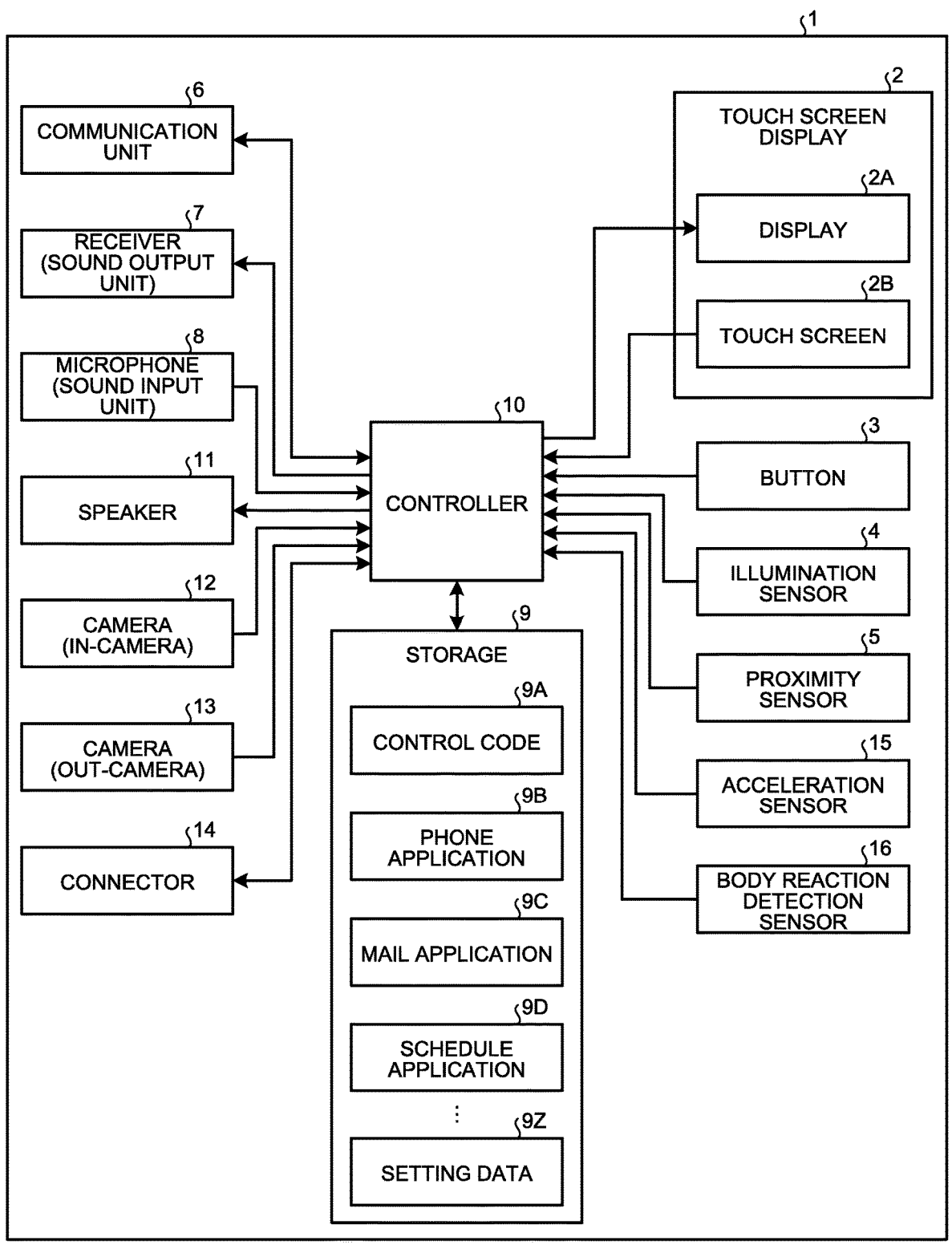
FIG. 1 is a block diagram illustrating an example of a functional configuration of a smartphone.

An example of a functional configuration of a smartphone 1 will be explained below. FIG. 1 is a block diagram illustrating an example of the functional configuration of the smartphone. In the description herein below, the same reference signs may be assigned to similar components. Moreover, overlapping explanation may be omitted.

As illustrated in FIG. 1, the smartphone 1 includes a touch screen display 2, a button 3, an illumination sensor 4, a proximity sensor 5, a communication unit 6, a receiver 7, a microphone 8, a storage 9, a controller 10, a speaker 11, a camera 12, a camera 13, a connector 14, an acceleration sensor 15, and a body reaction detection sensor 16.

The touch screen display 2 includes a display 2A and a touch screen 2B. For example, the display 2A and the touch screen 2B may be arranged in an overlapped manner, or may be arranged side by side, or may be arranged apart from each other. When the display 2A and the touch screen 2B are arranged in the overlapped manner, for example, one or more sides of the display 2A do not have to be along any of the sides of the touch screen 2B.

The display 2A includes a display device such as an LCD (Liquid Crystal Display), an OELD (Organic Electro-Luminescence Display), or an IELD (Inorganic Electro-Luminescence Display). The display 2A can display objects such as texts, images, symbols, and graphics within a screen. The screen including the objects displayed by the display 2A includes a screen called a lock screen, a screen called a home screen, and an application screen appearing during running of an application. The home screen is sometimes called a desktop, a standby screen, an idle screen, a standard screen, an application list screen, or a launcher screen.

The touch screen 2B can detect a contact of one or more fingers, one or more pens, or one or more stylus pens, etc. with the touch screen 2B. The touch screen 2B can detect positions where one or more fingers, one or more pens, or one or more stylus pens, etc. make contact with the touch screen 2B. The finger(s), the pen(s), and the stylus pen(s) detected by the touch screen 2B may be sometimes written as "finger(s)". The position(s) where the finger(s) detected by the touch screen 2B contacts or comes close to may be sometimes written as "detected position(s)". The touch screen 2B can notify the controller 10 of the contact of the finger with the touch screen 2B along with the position on the touch screen display 2 where it is contacted. The operation performed by the touch screen 2B can be performed by the touch screen display 2 having the touch screen 2B. In other words, the operation performed by the touch screen 2B may be performed by the touch screen display 2. An operation performed on the touch screen 2B can be rephrased as an operation performed on the touch screen display 2 having the touch screen 2B. An operation performed on the touch screen 2B can be rephrased as an operation performed on the smartphone 1 having the touch screen 2B.

The detection method of the touch screen 2B may be any detection method of a capacitive type detection method, a resistive type detection method, a surface acoustic wave type (or ultrasonic type) detection method, an infrared type detection method, an electromagnetic induction type detection method, and a load sensing type detection method. In the description herein below, for the sake of simplicity, it is assumed that a user uses his/her finger(s) to make contact with the touch screen 2B in order to operate the smartphone 1.

The controller 10 can determine a type of gestures based on at least one of the number of contacts detected by the touch screen 2B, a position where the contact is detected, a change of the position where the contact is detected, a temporal length over which the contact is detected, a time interval during which contacts are detected, and the number of detection times of the contacts. The operation performed by the controller 10 can be executed by the smartphone 1 having the controller 10. In other words, the operation performed by the controller 10 may be performed by the smartphone 1. The gesture is an operation performed on the touch screen 2B using the finger(s). Examples of the gestures determined by the controller 10 through the touch screen 2B include, but are not limited to, touch, long touch, release, swipe, tap, double tap, long tap, drag, flick, pinch in, and pinch out.

The button 3 receives an operation input from the user. When receiving an operation input from the user, the button 3 notifies the controller 10 of reception of the operation input. The number of buttons 3 may be one or more.

The illumination sensor 4 can detect illumination of the ambient light of the smartphone 1. The illumination indicates light intensity or brightness. The illumination sensor 4 may be used, for example, to adjust the luminance of the display 2A.

The proximity sensor 5 can detect the presence of nearby objects in a non-contact manner. The proximity sensor 5 can detect the presence of an object and a distance to the object based on, for example, infrared rays reflected from the object. The proximity sensor 5 may be used to detect that, for example, a user's face is brought close to the display 2A. The illumination sensor 4 and the proximity sensor 5 may be configured as one sensor. The proximity sensor 5 may be a sensor that detects the presence of an object and the distance to the object based on a change in the magnetic field or a change in the return time of the reflected ultrasonic wave, etc. instead of the infrared rays. The proximity sensor 5 may be any one of or an element integrated with some of the illumination sensor 4, the cameras 12 and 13, the touch screen 2B, and a touch switch, etc. The proximity sensor 5 is an example of the first sensor.

The communication unit 6 can perform wireless communication. The communication unit 6 supports a wireless communication standard. The wireless communication standard supported by the communication unit 6 includes, for example, a cellular-phone communication standard such as 2G, 3G, and 4G, and a short-range wireless communication standard. The cellular-phone communication standard includes, for example, LTE (Long Term Evolution), W-CDMA (Wideband Code Division Multiple Access), WiMAX (Worldwide Interoperability for Microwave Access), CDMA 2000, PDC (Personal Digital Cellular), GSM (registered trademark) (Global System for Mobile Communications), and PHS (Personal Handy-phone System). The short-range wireless communication standard includes, for example, IEEE 802.11 (IEEE is an abbreviation for The Institute of Electrical and Electronics Engineers, Inc.), Bluetooth (registered trademark), ZigBee (registered trademark), DECT (Digital Enhanced Cordless Telecommunications), Z-Wave, WiSun (Wireless Smart Utility Network), IrDA (Infrared Data Association), NFC (Near Field Communication), and WPAN (Wireless Personal Area Network). A WPAN communication standard includes, for example, ZigBee (registered trademark). The communication unit 6 may support one or more of the communication standards.

The receiver 7 is included in a sound output unit. The receiver 7 can output a sound signal transmitted from the controller 10 as sound. The receiver 7 may be used, for example, to output the voice of the other party on the phone. The microphone 8 is included in a sound input unit. The microphone 8 may be used to convert the voice of the user or the like to a sound signal and transmit the sound signal to the controller 10.

The storage 9 can store codes and data. The storage 9 may be used also as a work area that temporarily stores a processing result of the controller 10. The storage 9 may include any non-transitory storage medium such as a semiconductor storage medium and a magnetic storage medium. The storage 9 may include a plurality of types of storage mediums. The storage 9 may include a combination of a portable storage medium such as a memory card, an optical disc, or a magneto-optical disc with a reading device of the storage medium. The storage 9 may include a storage device used as a temporary storage area such as RAM (Random Access Memory).

Codes stored in the storage 9 include applications executed in the foreground or the background and a control code for assisting operations of the applications. For example, a screen for the application executed in the foreground is displayed on the display 2A. The control code includes, for example, an OS. The applications and the control code may be installed in the storage 9 through wireless communication by the communication unit 6 or through a non-transitory storage medium.

The storage 9 can store a control code 9A, a phone application 9B, a mail application 9C, a schedule application 9D, setting data 9Z, and the like.

The control code 9A may provide a function related to various types of control of the smartphone 1. The control code 9A may provide a function for determining whether the own device is in the storage part provided on the clothes, for example, when a proximity to the own device is detected by the first sensor and a body reaction is detected by the second sensor. The control code 9A may provide a function for determining that the own device is outside the storage part, for example, when the proximity to the own device is detected by the first sensor and the body reaction is not detected by the second sensor. The control code 9A may provide a function for determining that the own device is in the storage part, for example, on condition that the proximity to the own device is continuously detected by the first sensor after it is determined that the own device is in the storage part. The control code 9A may provide a function for determining that the own device is in the storage part, for example, on condition that the body reaction is continuously detected by the second sensor after it is determined that the own device is in the storage part. The control code 9A may provide a function for determining whether the own device is in the storage part, for example, when the smartphone 1 is in a sleep state. The control code 9A may provide a function for determining whether the own device is in the storage part, for example, on condition that the smartphone 1 transitions from an active state to the sleep state. The control code 9A may provide a function for determining whether the own device is in the storage part, for example, on condition that the smartphone 1 transitions from the sleep state to the active state. The control code 9A may provide a function for determining whether the own device is in the storage part, for example, on condition that a third sensor detects the change of a moving state of the own device. The control code 9A may provide a function for determining whether the own device is in the storage part, for example, on condition that an event occurs.

The phone application 9B may provide a phone call function for calling through wireless communication. The mail application 9C may provide an email function for composition, transmission, reception, display, and the like of emails. The schedule application 9D may provide a function for managing a schedule.

The setting data 9Z is configured to include various types of data used for processing performed by the control code 9A. The setting data 9Z includes, for example, a trigger condition for determining that the own device is in the storage part. The setting data 9Z includes a time condition for which the control code 9A determines that the proximity to the own device is continuously detected by the first sensor. The setting data 9Z includes a time condition for which the control code 9A determines that the body reaction is continuously detected by the second sensor.

The controller 10 includes a processor. Examples of the processor include, but are not limited to, a CPU (Central Processing Unit), an SoC (System-on-a-Chip), an MCU (Micro Control Unit), an FPGA (Field-Programmable Gate Array), and a coprocessor. The SoC may be integrated with other components such as the communication unit 6. The controller 10 can integrally control the operations of the smartphone 1. The various functions of the controller 10 can be implemented based on the control of the controller 10. The controller 10 is an example of the controller.

Specifically, the controller 10 can execute instructions included in the code stored in the storage 9. The controller 10 can refer to data stored in the storage 9 as necessary. The controller 10 can control function modules according to the data and the instructions. The controller 10 can implement various functions by controlling the function modules. Examples of the function modules include, but are not limited to, the display 2A, the communication unit 6, the microphone 8, and the speaker 11. The controller 10 can change the control according to a detection result of a detector. Examples of the detector include, but are not limited to, the touch screen 2B, the button 3, the illumination sensor 4, the proximity sensor 5, the microphone 8, the camera 12, the camera 13, the acceleration sensor 15, and the body reaction detection sensor 16.

The controller 10 executes the control code 9A, and may thereby implement the processing for determining that the own device is in the storage part provided on the clothes, for example, when a proximity to the own device is detected by the first sensor and a body reaction is detected by the second sensor. The controller 10 executes the control code 9A, and may thereby implement the processing for determining that the own device is outside the storage part, for example, when the proximity to the own device is detected by the first sensor and the body reaction is not detected by the second sensor. The controller 10 executes the control code 9A, and may thereby implement the processing for determining that the own device is in the storage part, for example, on condition that the proximity to the own device is continuously detected by the first sensor after it is determined that the own device is in the storage part. The controller 10 executes the control code 9A, and may thereby implement the processing for determining that the own device is in the storage part, for example, on condition that the body reaction is continuously detected by the second sensor after it is determined that the own device is in the storage part. The controller 10 executes the control code 9A, and may thereby perform determination as to whether the own device is in the storage part, for example, when the smartphone 1 is in the sleep state. The controller 10 executes the control code 9A, and may thereby perform determination as to whether the own device is in the storage part, for example, on condition that the smartphone 1 transitions from an active state to the sleep state. The controller 10 executes the control code 9A, and may thereby perform determination as to whether the own device is in the storage part, for example, on condition that the smartphone 1 transitions from the sleep state to the active state. The controller 10 executes the control code 9A, and may thereby perform determination as to whether the own device is in the storage part, for example, on condition that the third sensor detects the change of the moving state of the own device. The controller 10 executes the control code 9A, and may thereby perform determination as to whether the own device is in the storage part, for example, on condition that an event occurs.

The speaker 11 is included in the sound output unit. The speaker 11 can output a sound signal transmitted from the controller 10 as sound. The speaker 11 may be used to output, for example, a ring tone and music. Either one of the receiver 7 and the speaker 11 may serve as the other function.

The camera 12 and the camera 13 can convert a captured image to an electric signal. The camera 12 is an in-camera for capturing an object facing the display 2A. The camera 13 is an out-camera for capturing an object facing the opposite side of the display 2A. The camera 12 and the camera 13 may be mounted on the smartphone 1 in a state in which both of them are functionally and physically integrated as a camera unit that can be used by switching between the in-camera and the out-camera.

The connector 14 includes a terminal connected with other devices. The connector 14 may be a general-purpose terminal such as a USB (Universal Serial Bus), an HDMI (registered trademark) (High-Definition Multimedia Interface), Light Peak (Thunderbolt (registered trademark)), and an earphone/microphone connector. The connector 14 may be a dedicated terminal such as a dock connector. Examples of the devices connected to the connector 14 include, but are not limited to, an external storage, a speaker, and a communication device.

The acceleration sensor 15 can detect a direction and a magnitude of acceleration acting on the smartphone 1. The controller 10 can detect the change of the moving state of the smartphone 1 based on an acceleration pattern including a direction and a magnitude of acceleration detected by the acceleration sensor 15 or a time series change of the direction and the magnitude of acceleration.

The body reaction detection sensor 16 can detect a body reaction. The body reaction detection sensor 16 may detect a heart rate as a body reaction, may detect heart beats as a body reaction, or may detect an electric signal generated by the heart as a body reaction. The body reaction detection sensor 16 may use an infrared sensor or the like to detect the heart rate as a body reaction. The body reaction detection sensor 16 may use an acceleration sensor or the like to detect the heart beats as a body reaction. The body reaction detection sensor 16 may use a potential sensor or the like to detect the electric signal generated by the heart as a body reaction. The body reaction detection sensor 16 is an example of the second sensor.

The smartphone 1 may include a GPS receiver and a vibrator in addition to the function modules. The GPS receiver receives a radio signal of a predetermined frequency band from a GPS satellite, performs demodulation processing on the received radio signal, and transmits the processed signal to the controller 10. The vibrator vibrates part or whole of the smartphone 1. The vibrator includes, for example, a piezoelectric element or an eccentric motor in order to generate vibration. The smartphone 1 includes function modules such as a battery which should be used to maintain the functions of the smartphone 1.

FIGS. 2 to 8 are flowcharts illustrating a flow of processing performed by the smartphone 1. The processing illustrated in FIGS. 2 to 8 is implemented by the controller 10 executing the control code 9A or the like stored in the storage 9.

Figure 2:
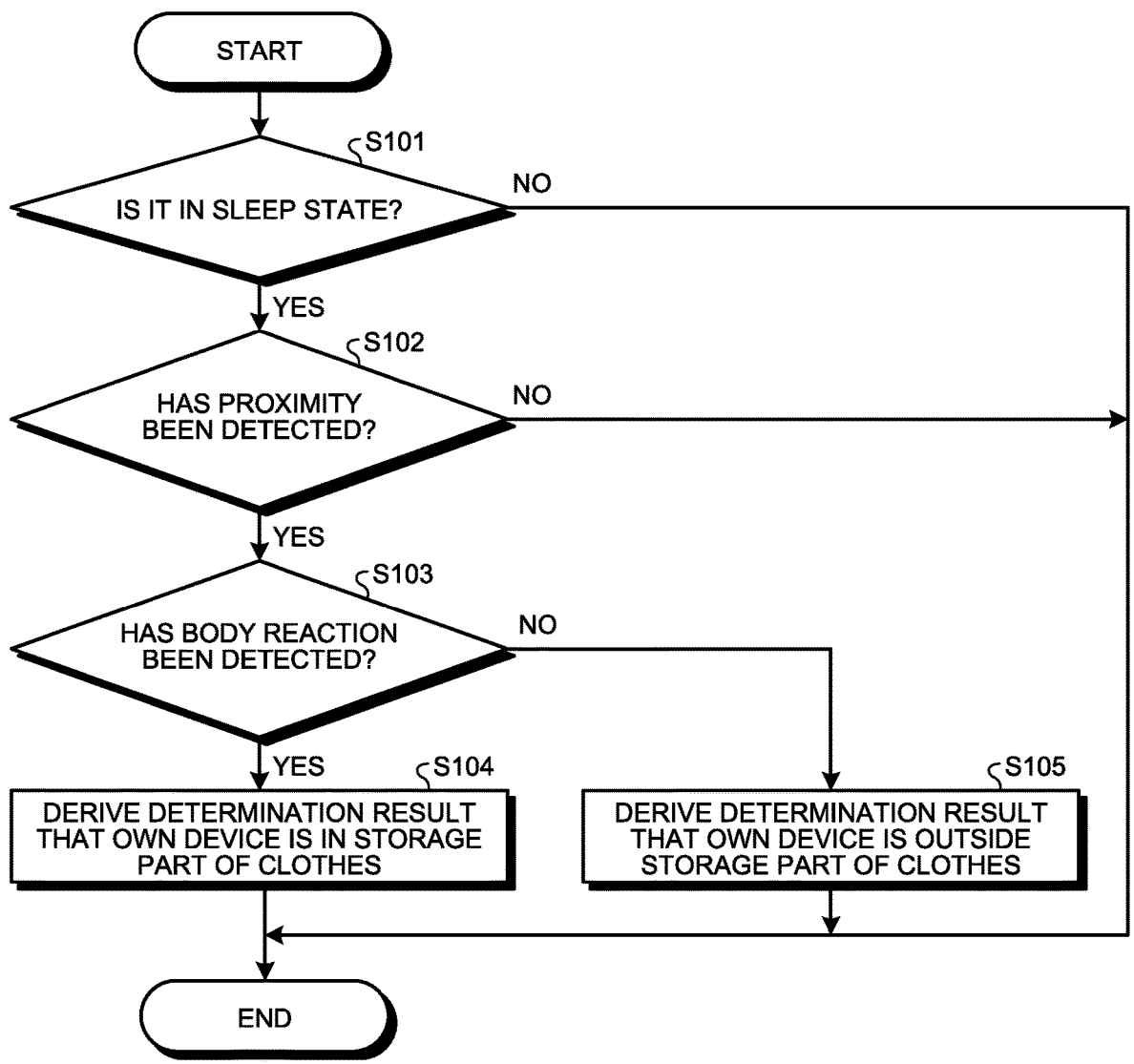
FIG. 2 is a flowchart illustrating an example of a flow of processing performed by the smartphone.

An example of the flow of the processing of the smartphone 1 that starts the processing by determining whether the own device is in a sleep state will be explained below with reference to FIG. 2. As illustrated in FIG. 2, the controller 10 determines whether the own device is in the sleep state (Step S101).

When it is determined that the own device is in the sleep state (Yes at Step S101), the controller 10 determines whether the proximity has been detected (Step S102).

When it is determined that the proximity has been detected (Yes at Step S102), the controller 10 determines whether the body reaction has been detected (Step S103).

When it is determined that the body reaction has been detected (Yes at Step S103), the controller 10 derives a determination result that the own device is in the storage part of the clothes (Step S104), and ends the processing illustrated in FIG. 2.

Meanwhile, when it is determined that the body reaction has not been detected (No at Step S103), the controller 10 derives a determination result that the own device is outside the storage part of the clothes (Step S105), and ends the processing illustrated in FIG. 2.

At Step S102, when it is determined that the proximity has not been detected (No at Step S102), the controller 10 ends the processing illustrated in FIG. 2.

At Step S101, when it is determined that the own device is not in the sleep state (No at Step S101), the controller 10 ends the processing illustrated in FIG. 2.

In the processing of FIG. 2, the sleep state may include all states in which the display 2A goes out. In the processing of FIG. 2, the controller 10 may detect at least one of the heart rate, the heart beats, and the electric signal generated by the heart as a body reaction. The same goes for the processing illustrated in FIG. 3 to FIG. 8.

Figure 3:
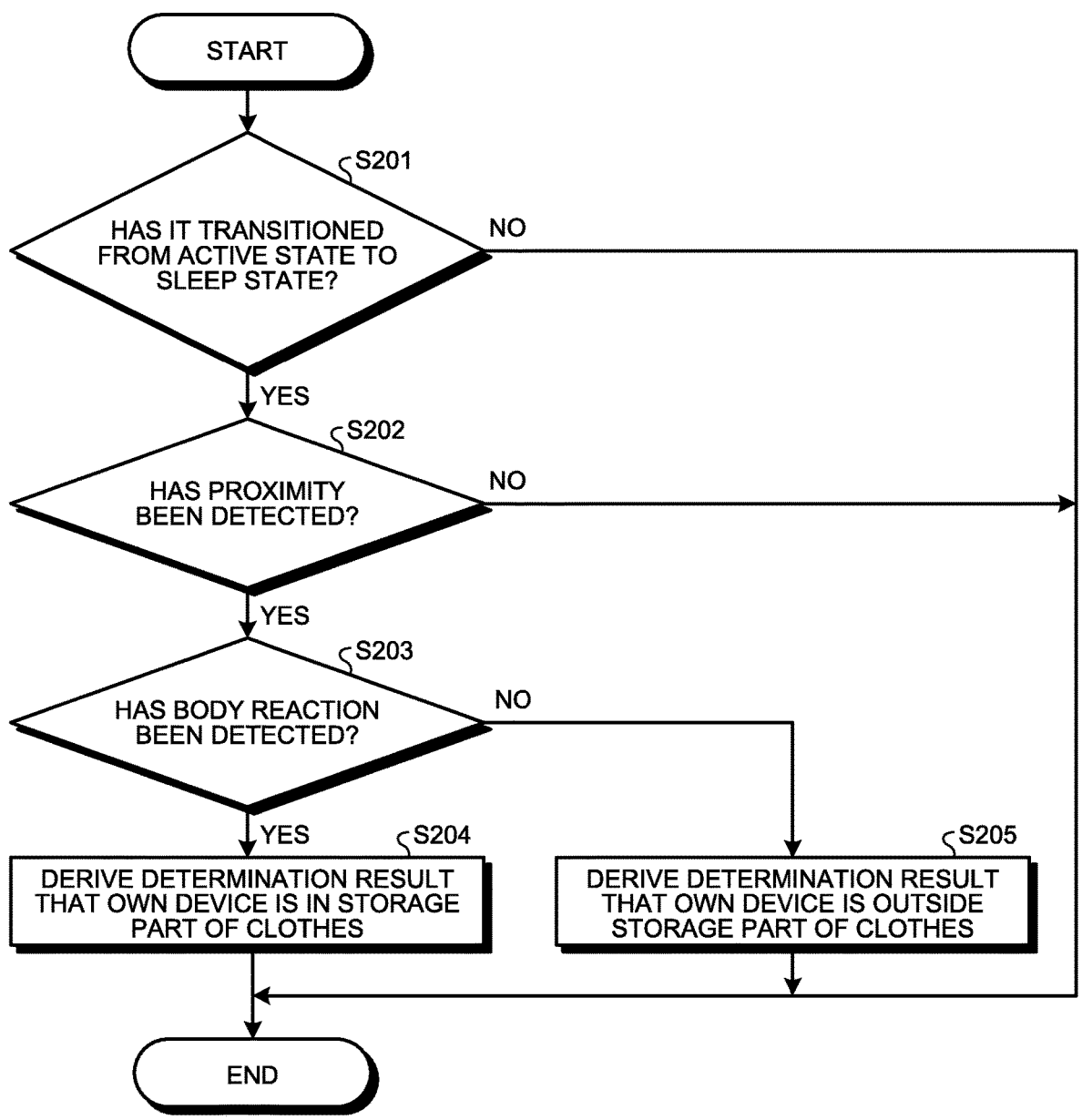
FIG. 3 is a flowchart illustrating an example of the flow of the processing performed by the smartphone.

An example of a flow of processing of the smartphone 1 that starts the processing triggered by transition from the active state to the sleep state of the own device will be explained below with reference to FIG. 3. As illustrated in FIG. 3, the controller 10 determines whether the own device has transitioned from the active state to the sleep state (Step S201).

When it is determined that the own device has transitioned from the active state to the sleep state (Yes at Step S201), the controller 10 determines whether the proximity has been detected (Step S202).

When it is determined that the proximity has been detected (Yes at Step S202), the controller 10 determines whether the body reaction has been detected (Step S203).

When it is determined that the body reaction has been detected (Yes at Step S203), the controller 10 derives a determination result that the own device is in the storage part of the clothes (Step S204), and ends the processing illustrated in FIG. 3.

Meanwhile, when it is determined that the body reaction has not been detected (No at Step S203), the controller 10 derives a determination result that the own device is outside the storage part of the clothes (Step S205), and ends the processing illustrated in FIG. 3.

At Step S202, when it is determined that the proximity has not been detected (No at Step S202), the controller 10 ends the processing illustrated in FIG. 3.

At Step S201, when it is determined that the own device has not transitioned from the active state to the sleep state (No at Step S201), the controller 10 ends the processing illustrated in FIG. 3.

Figure 4:
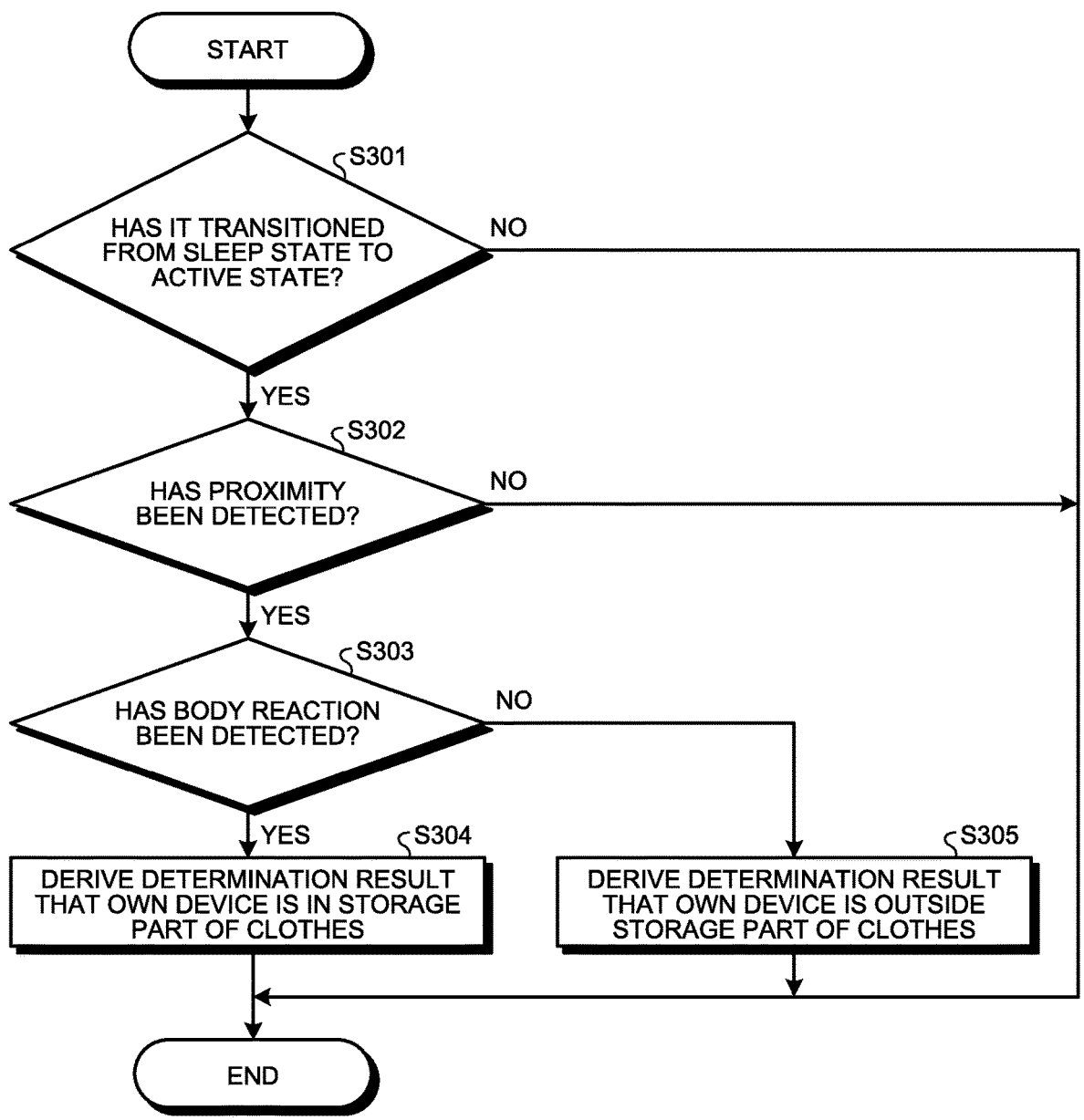
FIG. 4 is a flowchart illustrating an example of the flow of the processing performed by the smartphone.

An example of a flow of processing of the smartphone 1 that starts the processing triggered by transition from the sleep state to the active state of the own device will be explained below with reference to FIG. 4. As illustrated in FIG. 4, the controller 10 determines whether the own device has transitioned from the sleep state to the active state (Step S301).

When it is determined that the own device has transitioned from the sleep state to the active state (Yes at Step S301), the controller 10 determines whether the proximity has been detected (Step S302).

When it is determined that the proximity has been detected (Yes at Step S302), the controller 10 determines whether the body reaction has been detected (Step S303).

When it is determined that the body reaction has been detected (Yes at Step S303), the controller 10 derives a determination result that the own device is in the storage part of the clothes (Step S304), and ends the processing illustrated in FIG. 4.

Meanwhile, when it is determined that the body reaction has not been detected (No at Step S303), the controller 10 derives a determination result that the own device is outside the storage part of the clothes (Step S305), and ends the processing illustrated in FIG. 4.

At Step S302, when it is determined that the proximity has not been detected (No at Step S302), the controller 10 ends the processing illustrated in FIG. 4.

At Step S301, when it is determined that the own device has not transitioned from the sleep state to the active state (No at Step S301), the controller 10 ends the processing illustrated in FIG. 4.

In the processing of FIG. 4, the active state may include all states in which the display 2A is lit.

Figure 5:
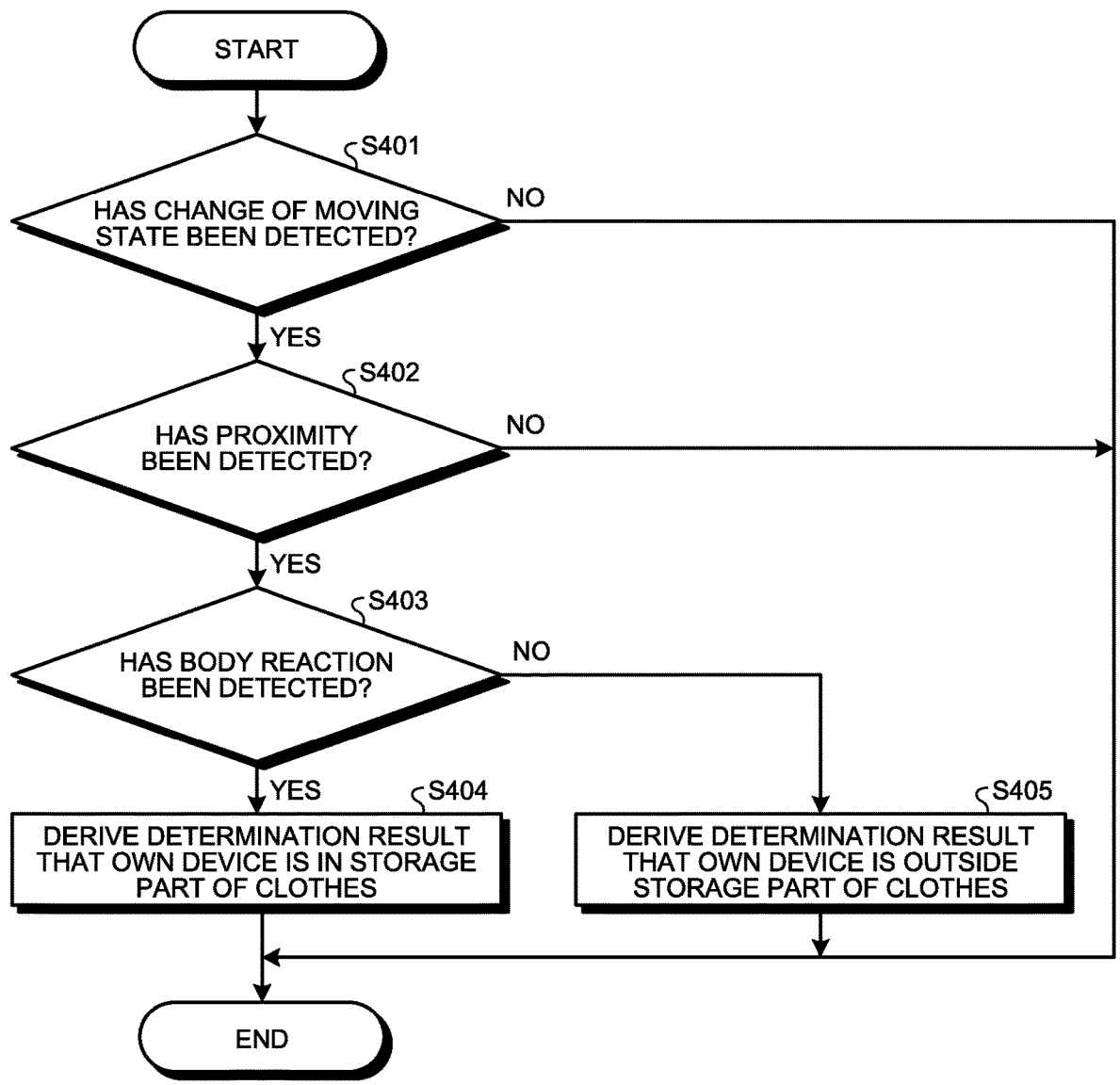
FIG. 5 is a flowchart illustrating an example of the flow of the processing performed by the smartphone.

An example of a flow of processing of the smartphone 1 that starts the processing triggered by change of the moving state of the own device will be explained below with reference to FIG. 5. As illustrated in FIG. 5, the controller 10 determines whether a change of the moving state of the own device has been detected (Step S401).

When it is determined that a change of the moving state of the own device has been detected (Yes at Step S401), the controller 10 determines whether the proximity has been detected (Step S402).

When it is determined that the proximity has been detected (Yes at Step S402), the controller 10 determines whether the body reaction has been detected (Step S403).

When it is determined that the body reaction has been detected (Yes at Step S403), the controller 10 derives a determination result that the own device is in the storage part of the clothes (Step S404), and ends the processing illustrated in FIG. 5.

Meanwhile, when it is determined that the body reaction has not been detected (No at Step S403), the controller 10 derives a determination result that the own device is outside the storage part of the clothes (Step S405), and ends the processing illustrated in FIG. 5.

At Step S402, when it is determined that the proximity has not been detected (No at Step S402), the controller 10 ends the processing illustrated in FIG. 5.

At Step S401, when it is determined that a change of the moving state of the own device has not been detected (No at Step S401), the controller 10 ends the processing illustrated in FIG. 5.

In the processing of FIG. 5, the change of the moving state of the own device includes a change from a stop state to a moving state and a change from a moving state to a stop state. In the processing of FIG. 5, the change of the moving state of the own device includes a change of a type of a vehicle.

Figure 6:
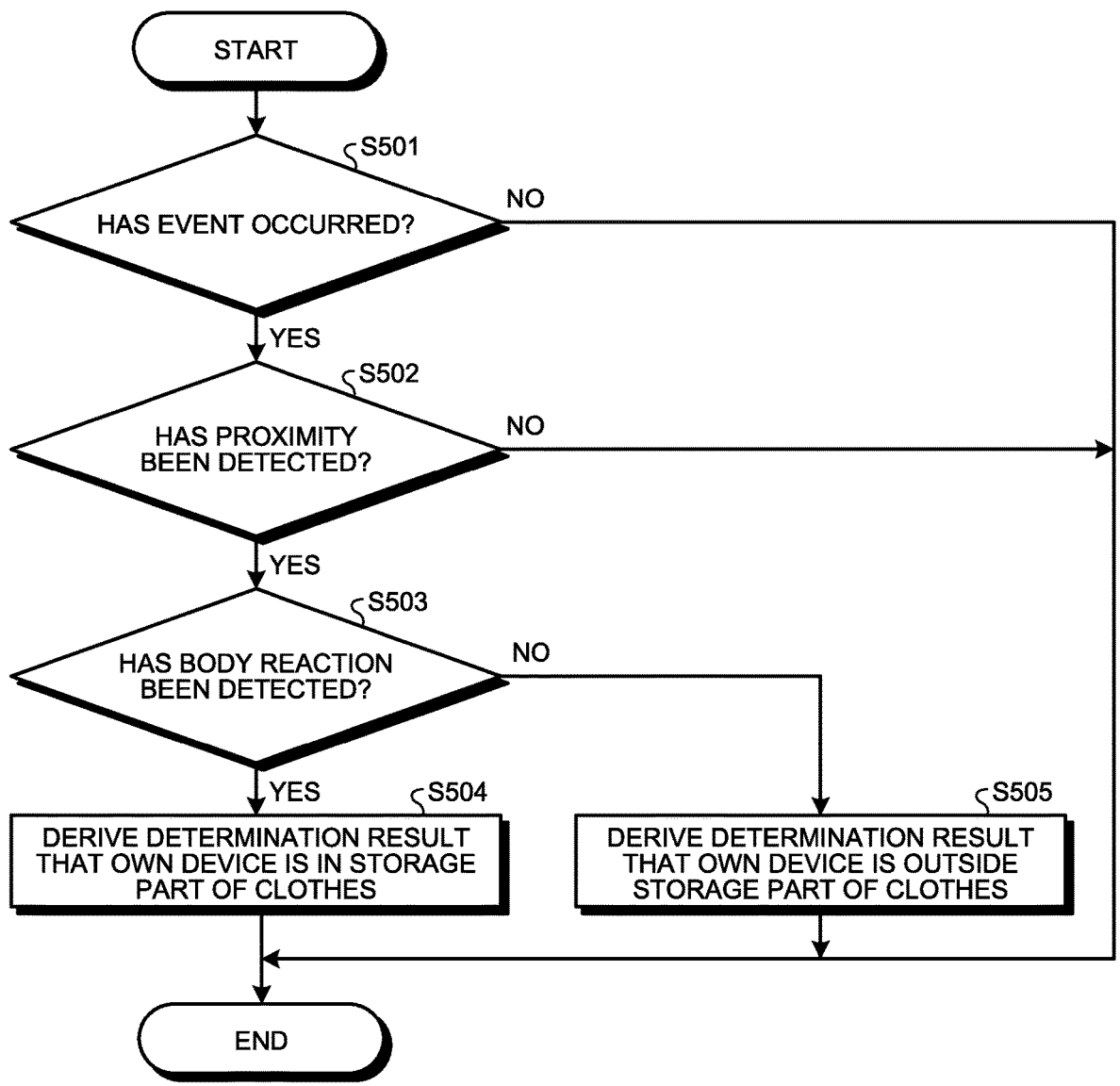
FIG. 6 is a flowchart illustrating an example of the flow of the processing performed by the smartphone.

An example of a flow of processing of the smartphone 1 that starts the processing triggered by occurrence of an event in the own device will be explained below with reference to FIG. 6. As illustrated in FIG. 6, the controller 10 determines whether an event has occurred (Step S501).

When it is determined that an event has occurred (Yes at Step S501), the controller 10 determines whether the proximity has been detected (Step S502).

When it is determined that the proximity has been detected (Yes at Step S502), the controller 10 determines whether the body reaction has been detected (Step S503).

When it is determined that the body reaction has been detected (Yes at Step S503), the controller 10 derives a determination result that the own device is in the storage part of the clothes (Step S504), and ends the processing illustrated in FIG. 6.

Meanwhile, when it is determined that the body reaction has not been detected (No at Step S503), the controller 10 derives a determination result that the own device is outside the storage part of the clothes (Step S505), and ends the processing illustrated in FIG. 6.

At Step S502, when it is determined that the proximity has not been detected (No at Step S502), the controller 10 ends the processing illustrated in FIG. 6.

At Step S501, when it is determined that an event has not occurred (No at Step S501), the controller 10 ends the processing illustrated in FIG. 6.

In the processing of FIG. 6, the event occurring in the own device includes pop-up notifications by various applications such as an incoming call, a mail reception notification by the mail application 9C, and a remind notification by the schedule application 9D.

Figure 7:
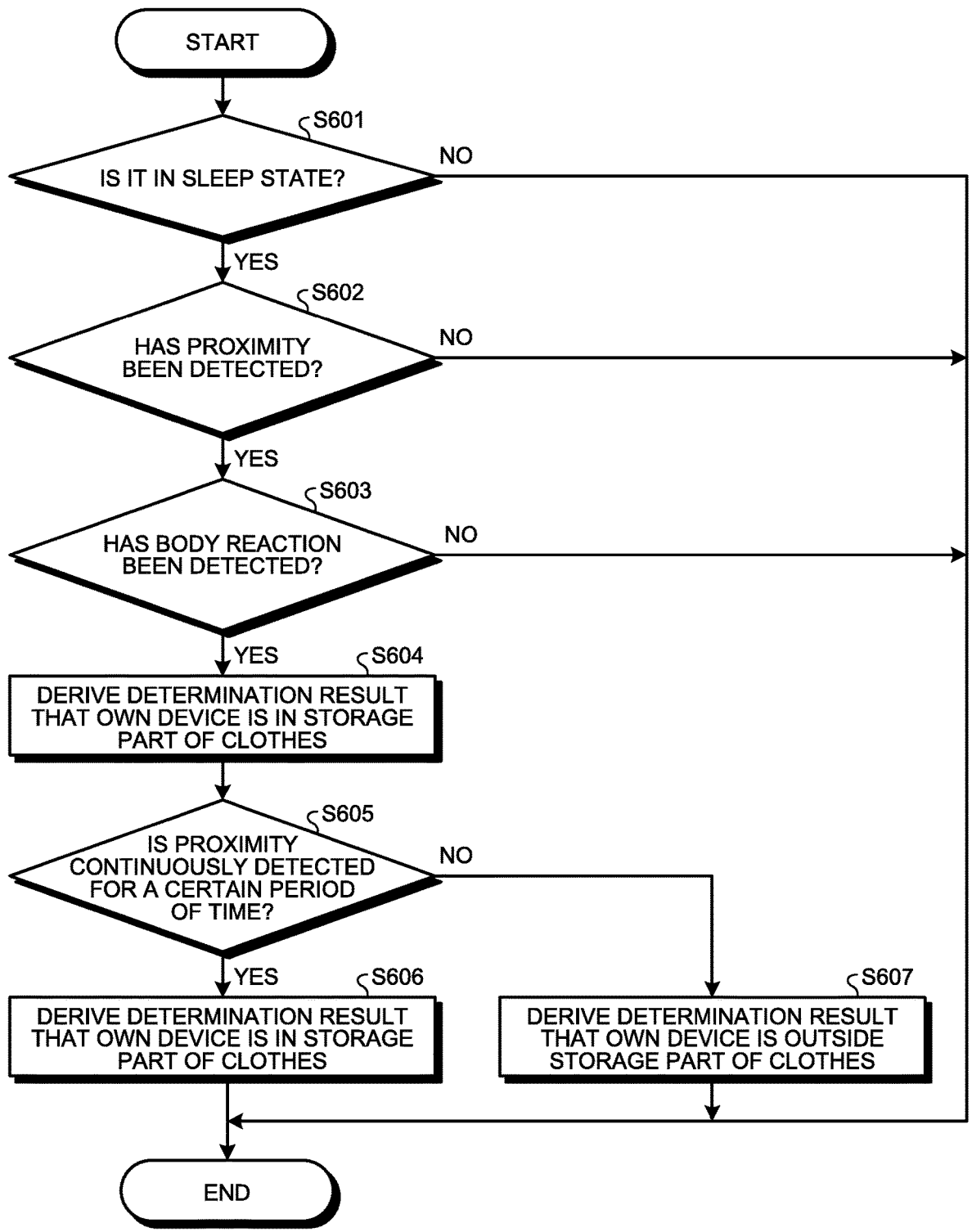
FIG. 7 is a flowchart illustrating an example of the flow of the processing performed by the smartphone.

An example of a flow of processing of the smartphone 1 that derives a result of determination as to whether the own device is in the storage part of the clothes on condition that the proximity is continuously detected for a certain period of time after the body reaction is detected will be explained below with reference to FIG. 7. As illustrated in FIG. 7, the controller 10 determines whether the own device is in the sleep state (Step S601).

When it is determined that the own device is in the sleep state (Yes at Step S601), the controller 10 determines whether the proximity has been detected (Step S602).

When it is determined that the proximity has been detected (Yes at Step S602), the controller 10 determines whether the body reaction has been detected (Step S603).

When it is determined that the body reaction has been detected (Yes at Step S603), the controller 10 derives a determination result that the own device is in the storage part of the clothes (Step S604).

Subsequently, the controller 10 determines whether the proximity is continuously detected for a certain period of time (Step S605).

When it is determined that the proximity is continuously detected for a certain period of time (Yes at Step S605), the controller 10 derives (maintains) a determination result that the own device is in the storage part of the clothes (Step S606), and ends the processing illustrated in FIG. 7.

Meanwhile, when the proximity is not continuously detected for a certain period of time (No at Step S605), the controller 10 derives a determination result that the own device is outside the storage part of the clothes (Step S607), and ends the processing illustrated in FIG. 7.

At Step S603, when it is determined that the body reaction has not been detected (No at Step S603), the controller 10 ends the processing illustrated in FIG. 7.

At Step S602, when it is determined that the proximity has not been detected (No at Step S602), the controller 10 ends the processing illustrated in FIG. 7.

At Step S601, when it is determined that the own device is not in the sleep state (No at Step S601), the controller 10 ends the processing illustrated in FIG. 7.

In the processing of FIG. 7, an arbitrary time can be set to a time condition in which time is set as a time during which the proximity is continuously detected. The processing illustrated in FIG. 7 can also be applied to the processing illustrated in FIG. 2 to FIG. 6.

Figure 8:
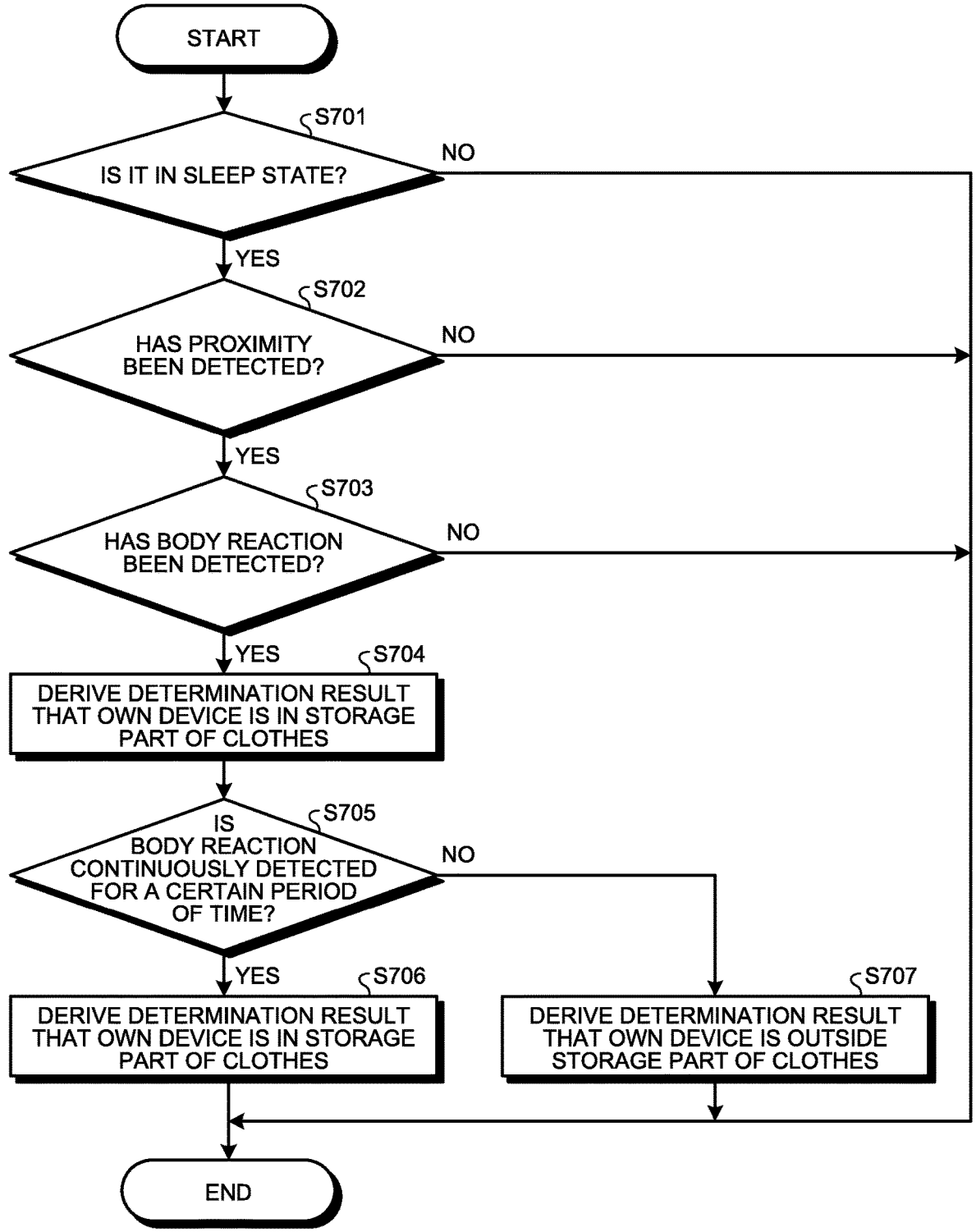
FIG. 8 is a flowchart illustrating an example of the flow of the processing performed by the smartphone.

An example of a flow of processing of the smartphone 1 that derives a result of determination as to whether the own device is in the storage part of the clothes on condition that the body reaction is continuously detected for a certain period of time after the body reaction is detected will be explained below with reference to FIG. 8. As illustrated in FIG. 8, the controller 10 determines whether the own device is in the sleep state (Step S701).

When it is determined that the own device is in the sleep state (Yes at Step S701), the controller 10 determines whether the proximity has been detected (Step S702).

When it is determined that the proximity has been detected (Yes at Step S702), the controller 10 determines whether the body reaction has been detected (Step S703).

When it is determined that the body reaction has been detected (Yes at Step S703), the controller 10 derives a determination result that the own device is in the storage part of the clothes (Step S704).

Subsequently, the controller 10 determines whether the body reaction is continuously detected for a certain period of time (Step S705).

When it is determined that the body reaction is continuously detected for a certain period of time (Yes at Step S705), the controller 10 derives (or maintains) a determination result that the own device is in the storage part of the clothes (Step S706), and ends the processing illustrated in FIG. 8.

Meanwhile, when the body reaction is not continuously detected for a certain period of time (No at Step S705), the controller 10 derives a determination result that the own device is outside the storage part of the clothes (Step S707), and ends the processing illustrated in FIG. 8.

At Step S703, when it is determined that the body reaction has not been detected (No at Step S703), the controller 10 ends the processing illustrated in FIG. 8.

At Step S702, when it is determined that the proximity has not been detected (No at Step S702), the controller 10 ends the processing illustrated in FIG. 8.

At Step S701, when it is determined that the own device is not in the sleep state (No at Step S701), the controller 10 ends the processing illustrated in FIG. 8.

In the processing of FIG. 8, an arbitrary time can be set to a time condition in which time is set as a time during which the body reaction is continuously detected.

When the body reaction is detected at the time of detection of the proximity, the smartphone 1 may derive a determination result that the own device is in the storage part of the clothes. Such a smartphone 1 can detect a situation that the own device is in the storage part of the clothes as a situation where the mobile electronic device is placed.

In the embodiments, the examples in which the smartphone 1 separately includes the proximity sensor 5 and the body reaction detection sensor 16 have been explained. An example in which the smartphone 1 functionally integrates the proximity sensor 5 and the body reaction detection sensor 16 will be explained in the following embodiments.

Figure 9:
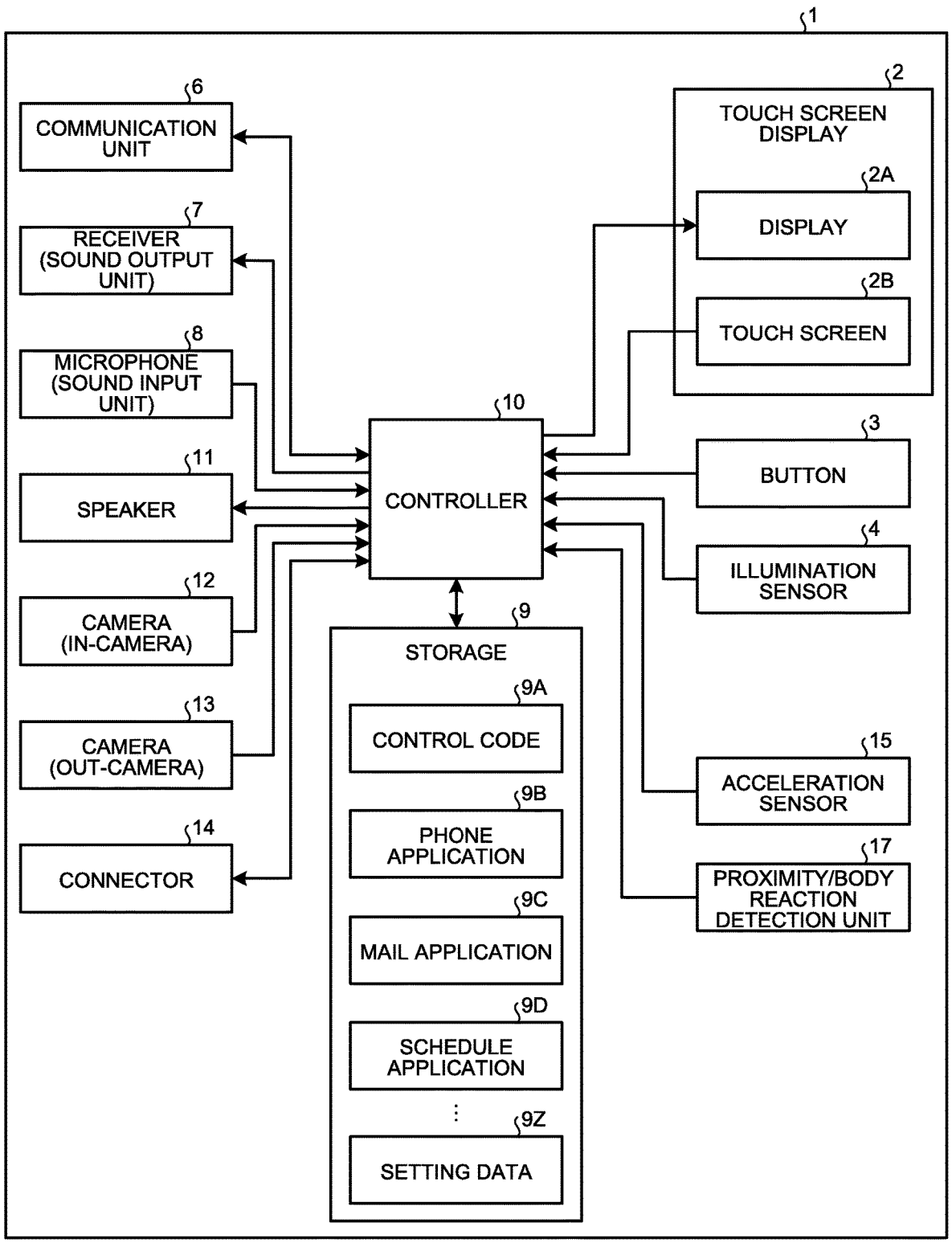
FIG. 9 is a block diagram illustrating an example of the functional configuration of the smartphone.

FIG. 9 is a block diagram illustrating an example of the functional configuration of the smartphone 1. In the following explanation, the same reference signs may be assigned to the similar components. In the following explanation, overlapping explanation may be omitted. In other words, the smartphone 1 may include the configurations and processing according to the embodiments even if they are not described in the following explanation.

The smartphone 1 includes a proximity/body reaction detection unit 17. The proximity/body reaction detection unit 17 can execute either one of detection of the proximity and detection of the body reaction under the control of the controller 10. An operating state of the proximity/body reaction detection unit 17 includes a proximity detection mode for detecting a proximity and a body detection mode for detecting a body reaction.

The control code 9A may provide a function for changing whether to cause the proximity/body reaction detection unit 17 to execute detection of a proximity or to execute detection of a body reaction.

The controller 10 executes the control code 9A, and may thereby implement the processing of changing whether to cause the proximity/body reaction detection unit 17 to execute detection of a proximity or to execute detection of a body reaction.

Figure 10:
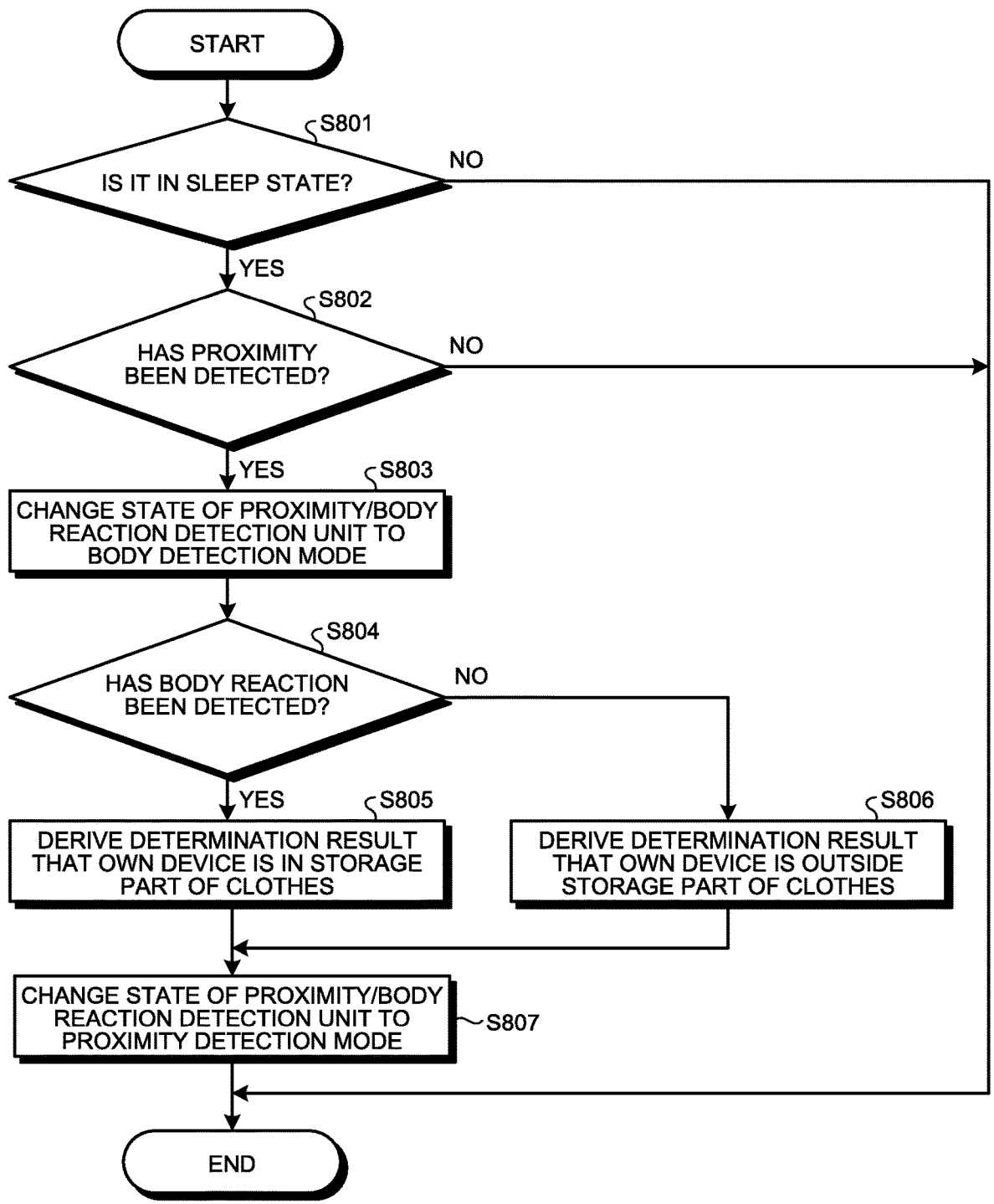
FIG. 10 is a flowchart illustrating an example of a flow of processing performed by the smartphone.

FIG. 10 is a flowchart illustrating an example of a flow of processing performed by the smartphone 1. The processing illustrated in FIG. 10 is implemented by the controller 10 executing the control code 9A or the like stored in the storage 9.

As illustrated in FIG. 10, the controller 10 determines whether the own device is in the sleep state (Step S801).

When it is determined that the own device is in the sleep state (Yes at Step S801), the controller 10 determines whether the proximity has been detected (Step S802).

When it is determined that the proximity has been detected (Yes at Step S802), the controller 10 changes the operating state of the proximity/body reaction detection unit 17 to the body detection mode (Step S803).

Subsequently, the controller 10 determines whether the body reaction has been detected (Step S804).

When it is determined that the body reaction has been detected (Yes at Step S804), the controller 10 derives a determination result that the own device is in the storage part of the clothes (Step S805). On the other hand, when it is determined that the body reaction has not been detected (No at Step S804), the controller 10 derives a determination result that the own device is outside the storage part of the clothes (Step S806).

Subsequently, the controller 10 changes the operating state of the proximity/body reaction detection unit 17 to the proximity detection mode (Step S807), and ends the processing illustrated in FIG. 10.

At Step S802, when it is determined that the proximity has not been detected (No at Step S802), the controller 10 ends the processing illustrated in FIG. 10.

At Step S801, when it is determined that the own device is not in the sleep state (No at Step S801), the controller 10 ends the processing illustrated in FIG. 10.

The smartphone 1 may cause the proximity/body reaction detection unit 17 to implement detection of a proximity and detection of a body reaction. The smartphone 1 having such a configuration can reduce the cost for implementation of the processing.

The smartphone 1 including the proximity/body reaction detection unit 17 may perform the processing for changing whether to cause the proximity/body reaction detection unit 17 to execute detection of a proximity or to execute detection of a body reaction.

A case, in which, when it is determined that the own device is in the storage part provided on the clothes, the smartphone 1 performs the processing for determining whether the clothes are upper-body clothing or lower-body clothing, will be explained below.

Figure 11:
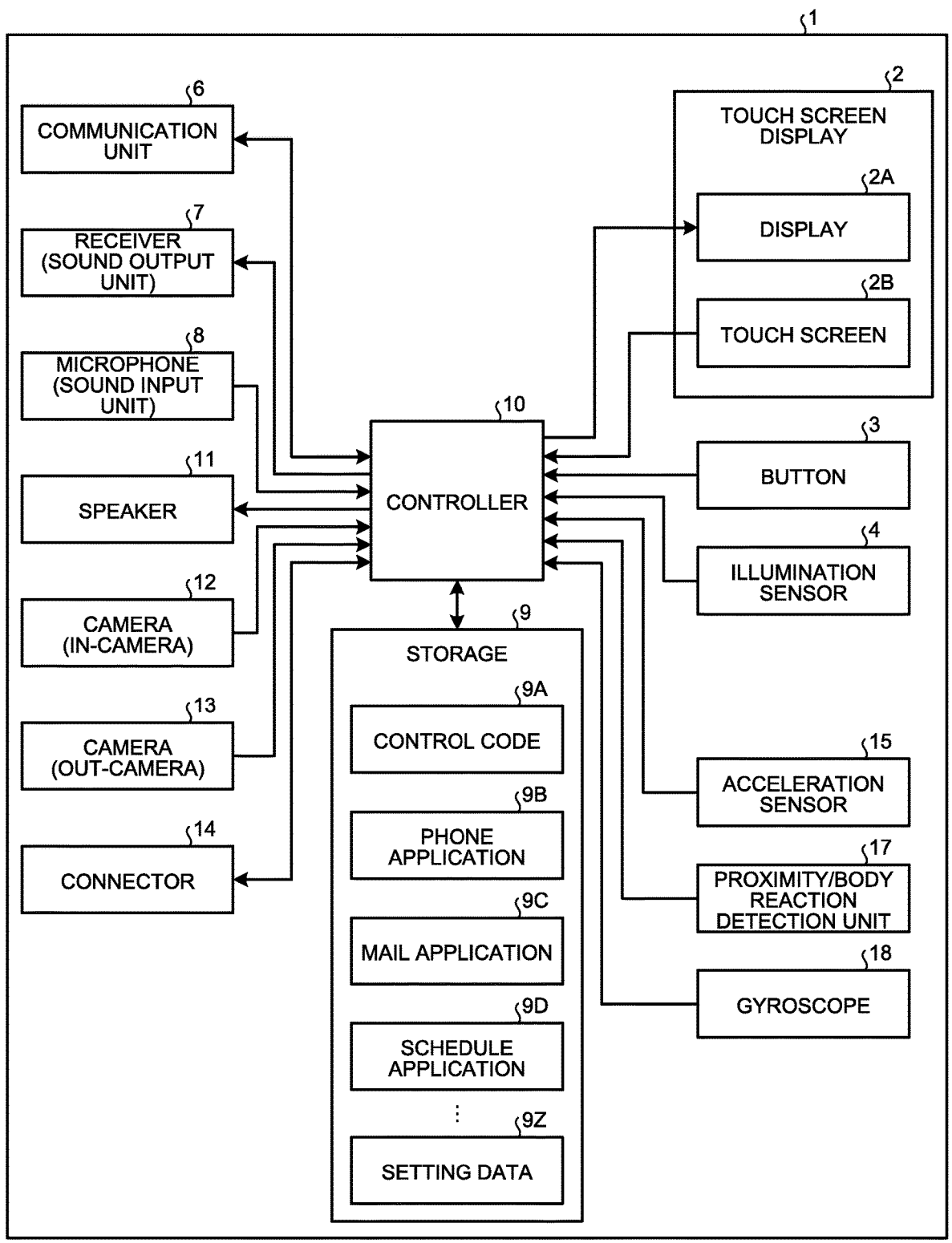
FIG. 11 is a block diagram illustrating an example of the functional configuration of the smartphone.

FIG. 11 is a block diagram illustrating an example of the functional configuration of the smartphone 1. In the following explanation, the same reference signs may be assigned to the similar components. In the following explanation, overlapping explanation may be omitted. In other words, the smartphone 1 may include the configurations and processing according to the embodiments even if they are not described in the following explanation.

A gyroscope 18 detects an angle and an angular velocity of the smartphone 1. The angle and the angular velocity are examples of rotation information.

The control code 9A can provide a function for determining whether the clothes correspond to either user's upper-body clothing or lower-body clothing based on the rotation information of the own device, for example, when it is determined that the own device (smartphone 1) is in the storage part provided on the clothes. Specifically, the control code 9A may determine whether the clothes correspond to either the upper-body clothing or the lower-body clothing based on motion patterns detected when the user is operating while the own device is in the storage part of his/her clothes. The motion patterns include a pattern detected when the own device is in the storage part of the upper-body clothing and a pattern detected when the own device is in the storage part of the lower-body clothing, which are different from each other, and each of which has its own unique pattern. The motion patterns may be prepared for use by measuring the smartphone 1 stored in the storage part of the upper-body clothing and in the storage part of the lower-body clothing. The motion pattern is configured based on data of an angular velocity detected by, for example, the gyroscope 18. The control code 9A may determine whether the clothes correspond to either the upper-body clothing or the lower-body clothing by checking the data detected by the gyroscope 18 against each of the motion patterns. The motion pattern is an example of the rotation information.

The setting data 9Z includes the data of the motion patterns.

For example, when it is determined that the own device is in the storage part provided on the clothes by executing the control code 9A, the controller 10 can implement the processing for determining whether the clothes correspond to either user's upper-body clothing or lower-body clothing based on the rotation information of the own device.

Figure 12:
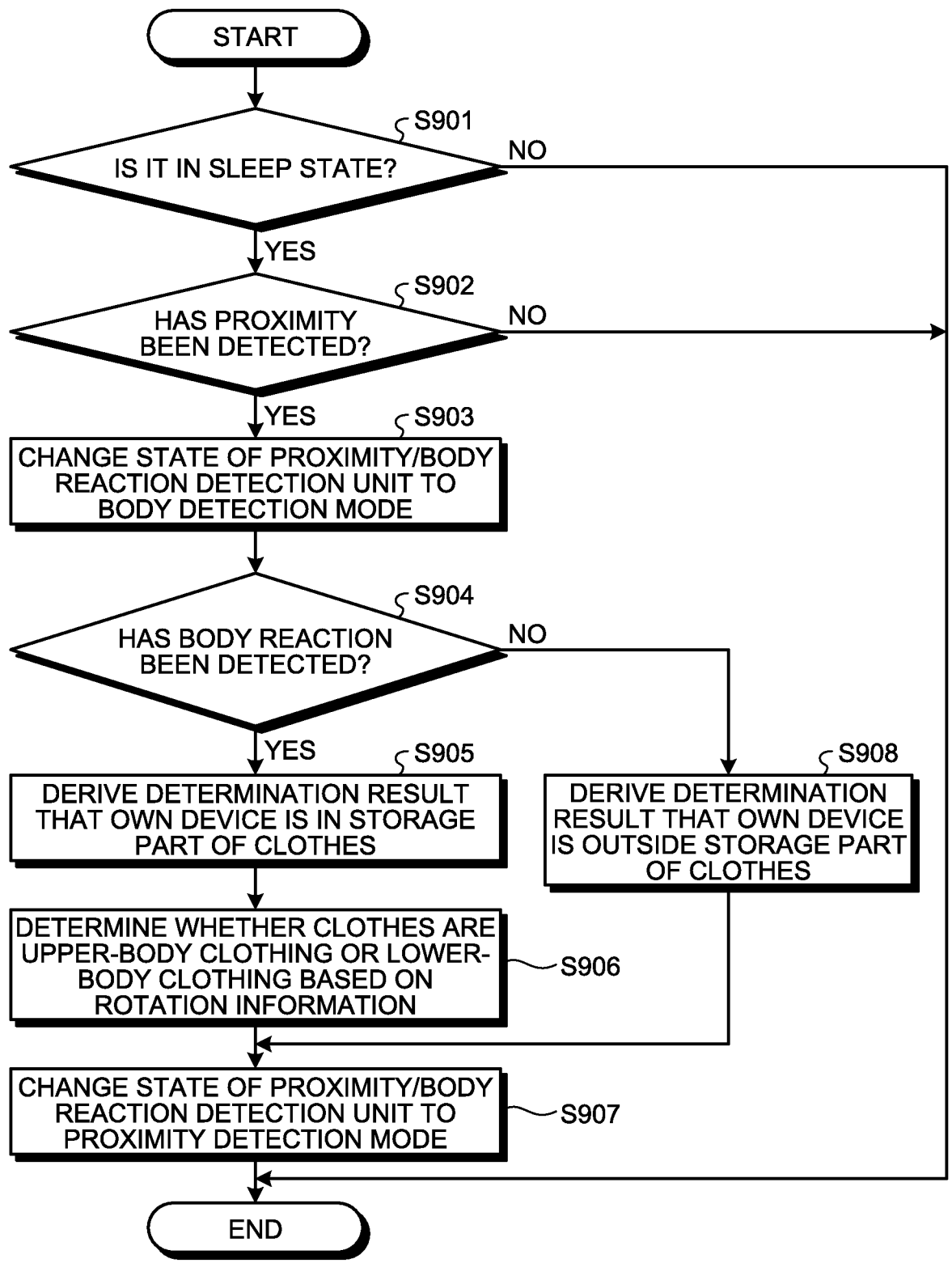
FIG. 12 is a flowchart illustrating an example of a flow of processing performed by the smartphone.

FIG. 12 is a flowchart illustrating an example of a flow of processing performed by the smartphone 1. The processing illustrated in FIG. 12 is implemented by the controller 10 executing the control code 9A or the like stored in the storage 9.

As illustrated in FIG. 12, the controller 10 determines whether the own device is in the sleep state (Step S901).

When it is determined that the own device is in the sleep state (Yes at Step S901), the controller 10 determines whether the proximity has been detected (Step S902).

When it is determined that the proximity has been detected (Yes at Step S902), the controller 10 changes the operating state of the proximity/body reaction detection unit 17 to the body detection mode (Step S903).

Subsequently, the controller 10 determines whether the body reaction has been detected (Step S904).

When it is determined that the body reaction has been detected (Yes at Step S904), the controller 10 derives a determination result that the own device is in the storage part of the clothes (Step S905).

The controller 10 then determines whether the clothes are the upper-body clothing or the lower-body clothing based on the rotation information (Step S906).

Subsequently, the controller 10 changes the operating state of the proximity/body reaction detection unit 17 to the proximity detection mode (Step S907), and ends the processing illustrated in FIG. 12.

At Step S904, when it is determined that the body reaction has not been detected (No at Step S904), the controller 10 derives a determination result that the own device is outside the storage part of the clothes (Step S908), and proceeds to the procedure of Step S907.

At Step S902, when it is determined that the proximity has not been detected (No at Step S902), the controller 10 ends the processing illustrated in FIG. 12.

At Step S901, when it is determined that the own device is not in the sleep state (No at Step S901), the controller 10 ends the processing illustrated in FIG. 12.

The smartphone 1 may change a notification mode according to whether the clothes are the upper-body clothing or the lower-body clothing. In the following explanation, the same reference signs may be assigned to the similar components. In the following explanation, overlapping explanation may be omitted. In other words, the smartphone 1 may include the configurations and processing according to the embodiments even if they are not described in the following explanation.

The control code 9A may provide a function for changing a mode of notification to the user according to cases where it is determined that the clothes with the storage part in which the own device is stored are the upper-body clothing and where it is determined that the clothes are the lower-body clothing. The control code 9A may provide a function for making greater an output intensity of notification by vibration that is executed, for example, when the clothes are determined as the upper-body clothing than an output intensity of notification by vibration executed when the clothes are determined as the lower-body clothing. Alternatively, the control code 9A may provide a function for performing settings so as to make longer an output time of notification by vibration that is executed, for example, when the clothes are determined as the upper-body clothing than an output time of notification by vibration executed when the clothes are determined as the lower-body clothing.

The controller 10 executes the control code 9A, and may thereby implement the processing for changing the mode of notification to the user according to cases in which it is determined that the clothes with the storage part in which the own device is stored are the upper-body clothing and in which it is determined that the clothes are the lower-body clothing.

Figure 13:
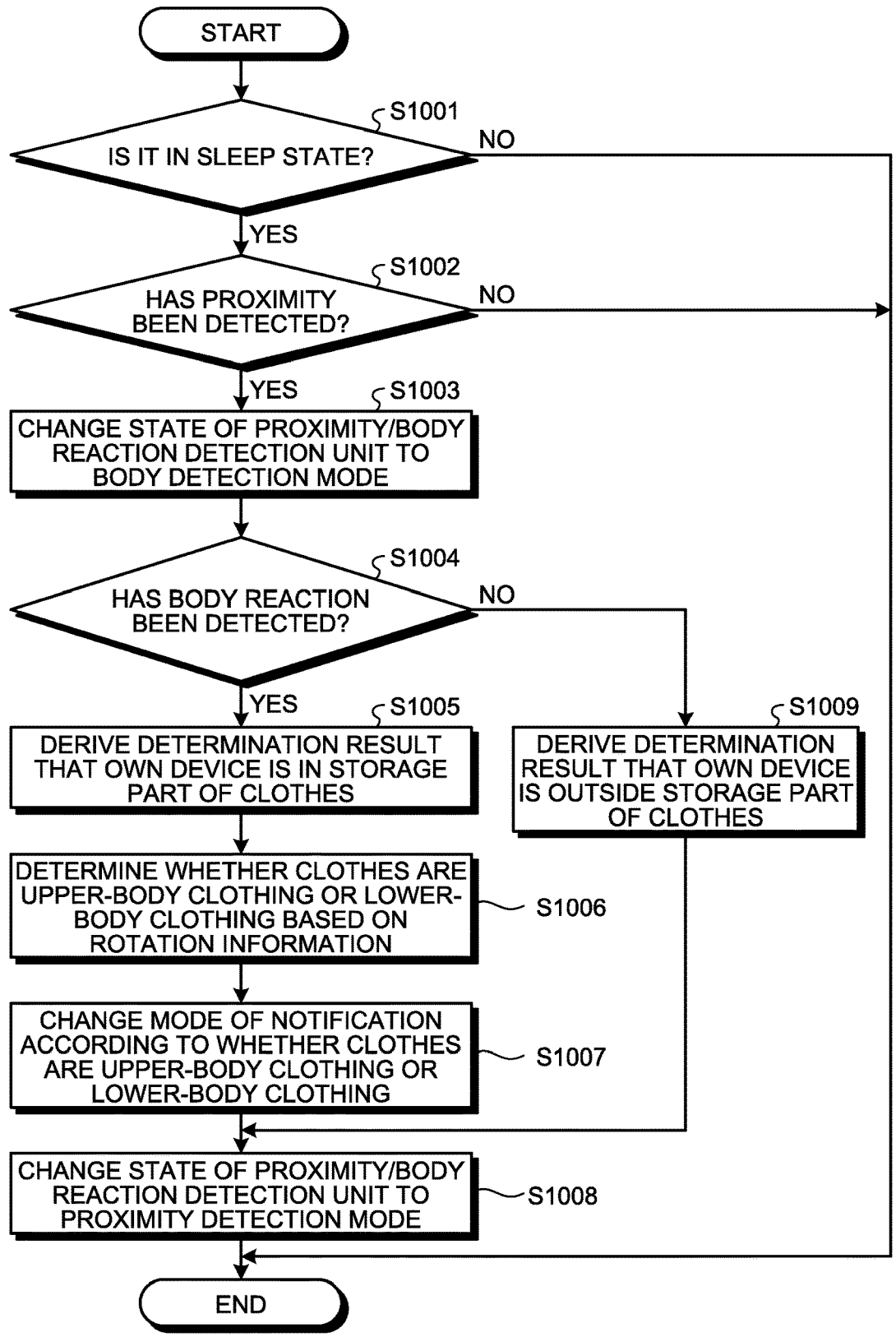
FIG. 13 is a flowchart illustrating an example of the flow of the processing performed by the smartphone.

FIG. 13 is a flowchart illustrating an example of the flow of processing performed by the smartphone 1. The processing illustrated in FIG. 13 is implemented by the controller 10 executing the control code 9A or the like stored in the storage 9.

As illustrated in FIG. 13, the controller 10 determines whether the own device is in the sleep state (Step S1001).

When it is determined that the own device is in the sleep state (Yes at Step S1001), the controller 10 determines whether the proximity has been detected (Step S1002).

When it is determined that the proximity has been detected (Yes at Step S1002), the controller 10 changes the operating state of the proximity/body reaction detection unit 17 to the body detection mode (Step S1003).

Subsequently, the controller 10 determines whether the body reaction has been detected (Step S1004).

When it is determined that the body reaction has been detected (Yes at Step S1004), the controller 10 derives a determination result that the own device is in the storage part of the clothes (Step S1005).

The controller 10 then determines whether the clothes are the upper-body clothing or the lower-body clothing based on the rotation information (Step S1006).

Subsequently, the controller 10 changes the mode of notification according to the determination result of Step S1006, i.e., according to whether the clothes are the upper-body clothing or the lower-body clothing (Step S1007). For example, when the setting is made to perform notification by vibration, the controller 10 makes greater an output intensity of notification by vibration executed when the clothes are determined as the upper-body clothing than an output intensity of notification by vibration executed when the clothes are determined as the lower-body clothing. Alternatively, the controller 10 makes longer an output time of notification by vibration that is executed, for example, when the clothes are determined as the upper-body clothing than an output time of notification by vibration executed when the clothes are determined as the lower-body clothing.

Subsequently, the controller 10 changes the operating state of the proximity/body reaction detection unit 17 to the proximity detection mode (Step S1008), and ends the processing illustrated in FIG. 13.

At Step S1004, when it is determined that the body reaction has not been detected (No at Step S1004), the controller 10 derives a determination result that the own device is outside the storage part of the clothes (Step S1009), and proceeds to the procedure of Step S1008.

At Step S1002, when it is determined that the proximity has not been detected (No at Step S1002), the controller 10 ends the processing illustrated in FIG. 13.

At Step S1001, when it is determined that the own device is not in the sleep state (No at Step S1001), the controller 10 ends the processing illustrated in FIG. 13.

In the embodiments, the smartphone 1 may determine whether the user is in a standing state (standing position) or in a sitting state (sitting position) based on the direction of acceleration acting on the own device (smartphone 1) and the direction of gravitational acceleration. In the following explanation, the same reference signs may be assigned to the similar components. In the following explanation, overlapping explanation may be omitted. In other words, the smartphone 1 may include the configurations and processing according to the embodiments even if they are not described in the following explanation.

The control code 9A may provide a function for determining whether the own device is in a first state or in a second state when the rotation of the own device is detected based on the rotation information after it is determined that the clothes with the storage part in which the own device is stored are the lower-body clothing. The first state is a user standing state. The second state is a user sitting state. The control code 9A should determine whether the user is in the first state or in the second state based on the direction of acceleration acting on the own device upon detecting the rotation and the direction of gravitational acceleration. Specifically, when the direction of acceleration acting on the own device is opposite to the direction of gravitational acceleration, the control code 9A should determine that the user is in the first state in which the user is standing. On the other hand, when the direction of acceleration acting on the own device is the same as the direction of gravitational acceleration, the control code 9A should determine that the user is in the second state in which the user is sitting.

When the control code 9A is executed to determine that the clothes with the storage part in which the own device is stored are the lower-body clothing and thereafter the rotation of the own device is detected based on the rotation information, the controller 10 can implement the processing for determining whether the user is in the first state in which the user is standing or in the second state in which the user is sitting based on the direction of acceleration acting on the own device upon detecting the rotation and the direction of gravitational acceleration. In order that the user changes the own state from the standing position to the sitting position or from the sitting position to the standing position, it is necessary for the user to bend his/her legs or to stretch the legs (i.e. bending and stretching exercises of legs). At this time, user's thighs rotate around his/her hip joints. Because the lower-body clothing has a storage part that is generally provided somewhere near the thigh, when the own device is stored in the storage part of the lower-body clothing, the own device is fixed to somewhere near the thigh of the user by the storage part. Therefore, when the user's state changes to either the standing position or the sitting position, the own device rotates with a rotation of the thighs. In other words, when the smartphone 1 determines that the clothes with the storage part in which the own device is stored are the lower-body clothing and thereafter detects the rotation of the own device, there is a possibility that the user's state has changed to either the standing position or the sitting position. Moreover, when it is determined that the clothes with the storage part in which the own device is stored are the lower-body clothing and thereafter the rotation of the own device is detected, there is a case where the user is walking or running in addition to the case where the user's state changes to either the standing position or the sitting position. In order to more accurately determine whether the detected rotation of the own device is caused by the change of the user's state to the standing position or to the sitting position, it may be determined based on the acceleration parallel to the direction of gravity acting on the own device upon detecting the rotation of the own device. Specifically, regarding the acceleration parallel to the direction of gravity acting on the own device when the rotation of the own device is detected, the case where the user's state changes either to the standing position or to the sitting position is greater than the case where the user is walking or running, and by using this fact, a determination condition may be provided to determine in which of the cases the rotation of the own device occurs. In addition, by determining whether the own device is accelerated in the direction of gravitational acceleration or in the opposite direction to the direction of gravitational acceleration based on the direction of acceleration acting on the own device upon detecting the rotation and the direction of gravitational acceleration, it is possible to determine whether the rotation of the own device is detected by the change of the user's state from the standing position to the sitting position or by the change thereof from the sitting position to the standing position. The rotation of the own device, which is detected based on the rotation information after the determination that the clothes with the storage part in which the own device is stored are the lower-body clothing, is a unidirectional rotation of the own device calculated by values detected by, for example, a three-axis angular velocity sensor. Here, it is possible to increase determination accuracy of the user's current state (standing position or sitting position) by setting a range condition of a rotation angle of the own device for determining that the rotation is detected due to either the change from the user's standing position to the sitting position or from the sitting position to the standing position, to a range condition obtained by excluding the range of the rotation angle of the own device detected when the user is walking or running from the range condition. In order to increase the determination accuracy of the user's current state (standing position or sitting position), after it is determined whether the user is in the standing state or in the sitting state, the user's current state (standing position or sitting position) may be determined according to the duration of the determined state. Specifically, when the user is walking or running, the rotation of the thighs is repeated, and therefore, if the determination as to whether the user is in the standing state or in the sitting state continues for a predetermined period of time, it may be determined that the state continuously determined is the user's current state (standing position or sitting position). Moreover, by previously storing detection patterns of acceleration detected when the user is walking or running in the smartphone 1 and by checking the data of acceleration acting on the own device when the rotation of the own device is detected against the detection patterns of the acceleration, it may be determined that the rotation of the own device is detected in either of the cases where the user's state changes to the standing state or to the sitting state.

Figure 14A:
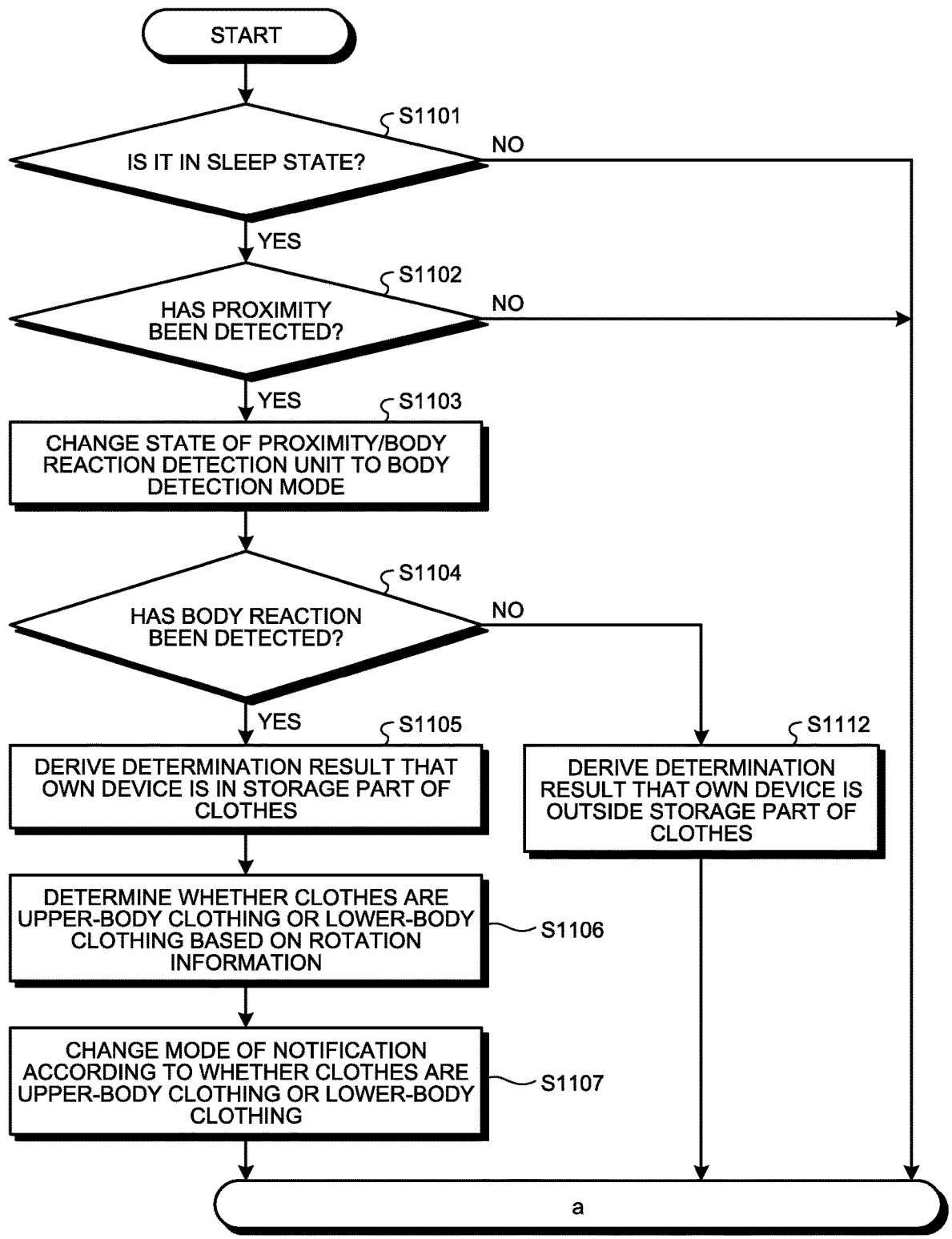
FIG. 14A is a flowchart illustrating an example of the flow of the processing performed by the smartphone.
Figure 14B:
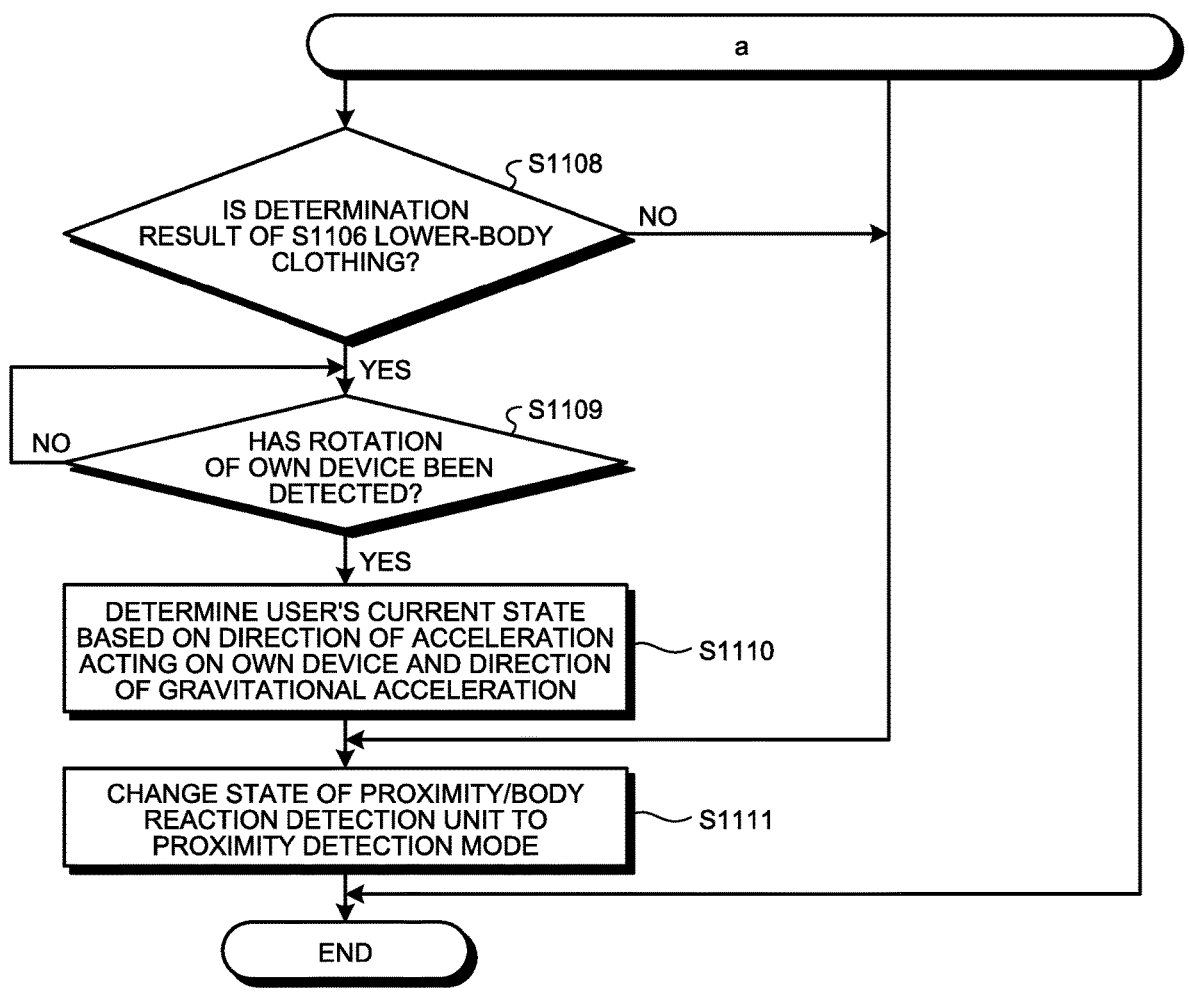
FIG. 14B is a flowchart illustrating an example of the flow of the processing performed by the smartphone.

FIG. 14A and FIG. 14B are flowcharts illustrating an example of the flow of the processing performed by the smartphone 1. The processing illustrated in FIG. 14A and FIG. 14B is implemented by the controller 10 executing the control code 9A or the like stored in the storage 9.

As illustrated in FIG. 14A and FIG. 14B, the controller 10 determines whether the own device is in the sleep state (Step S1101).

When it is determined that the own device is in the sleep state (Yes at Step S1101), the controller 10 determines whether the proximity has been detected (Step S1102).

When it is determined that the proximity has been detected (Yes at Step S1102), the controller 10 changes the operating state of the proximity/body reaction detection unit 17 to the body detection mode (Step S1103).

Subsequently, the controller 10 determines whether the body reaction has been detected (Step S1104).

When it is determined that the body reaction has been detected (Yes at Step S1104), the controller 10 derives a determination result that the own device is in the storage part of the clothes (Step S1105).

The controller 10 then determines whether the clothes are the upper-body clothing or the lower-body clothing based on the rotation information (Step S1106).

Subsequently, the controller 10 changes the mode of notification according to the determination result of Step S1106, i.e., according to whether the clothes are the upper-body clothing or the lower-body clothing (Step S1107).

The controller 10 then determines whether the determination result of Step S1106 is a determination result of "lower-body clothing" (Step S1108).

When the determination result of "lower-body clothing" has been derived by the determination of Step S1106 (Yes at Step S1108), the controller 10 determines whether the rotation of the own device has been detected based on the rotation information (Step S1109). When it is determined that the rotation of the own device has not been detected (No at Step S1109), the controller 10 repeats the determination of Step S1109.

Meanwhile, when it is determined that the rotation of the own device has been detected (Yes at Step S1109), the controller 10 determines the user's current state (standing position or sitting position) based on the direction of acceleration acting on the own device upon detecting the rotation and the direction of gravitational acceleration (Step S1110).

Subsequently, the controller 10 changes the operating state of the proximity/body reaction detection unit 17 to the proximity detection mode (Step S1111), and ends the processing illustrated in FIG. 14A and FIG. 14B.

At Step S1108, when the determination result of "lower-body clothing" has not been derived by the determination of Step S1106 (No at Step S1108), the controller 10 proceeds to the procedure of Step S1111.

At Step S1104, when it is determined that the body reaction has not been detected (No at Step S1104), the controller 10 derives a determination result that the own device is outside the storage part of the clothes (Step S1112), and proceeds to the procedure of Step S1111.

At Step S1102, when it is determined that the proximity has not been detected (No at Step S1102), the controller 10 ends the processing illustrated in FIG. 14A and FIG. 14B.

At Step S1101, when it is determined that the own device is not in the sleep state (No at Step S1101), the controller 10 ends the processing illustrated in FIG. 14A and FIG. 14B.

When it is determined that the user is in the sitting state by the processing illustrated in FIG. 14A and FIG. 14B, the smartphone 1 can determine that the user is in the standing state before the determination. On the other hand, when it is determined that the user is in the standing state by the processing illustrated in FIG. 14A and FIG. 14B, the smartphone 1 can determine that the user is in the sitting state before the determination.

In the embodiments, the smartphone 1 may calculate the amount of activity of the user according to his/her state. In the following explanation, the same reference signs may be assigned to the similar components. In the following explanation, overlapping explanation may be omitted. In other words, the smartphone 1 may include the configurations and processing according to the embodiments even if they are not described in the following explanation.

The control code 9A may provide a function for calculating the amount of activity of the user based on the result of determination as to whether the user is in the first state in which the user is standing or in the second state in which the user is sitting. The control code 9A calculates the amount of activity of the user by using, for example, METs (Metabolic equivalents) corresponding to the user's state. The METs is a unit of physical activity indicating how many times the energy consumption by exercise is greater than the energy consumption at rest. The control code 9A can calculate the amount of activity by the product (METs×Time) of the value of METs corresponding to the user's state (e.g., standing position or sitting position) and the duration of physical activity. The control code 9A may calculate, as a value indicating the amount of activity of the user, a value directly representing the amount of activity of the user such as walking distance, or may calculate a value indirectly representing the amount of activity of the user such as calorie consumption and food corresponding to the calorie consumption.

The setting data 9Z includes the data of METs corresponding to the user's state.

The controller 10 executes the control code 9A, and can thereby implement the processing of calculating the amount of activity of the user based on the result of determination as to whether the user is in the first state in which the user is standing or in the second state in which the user is sitting.

Figure 15A:
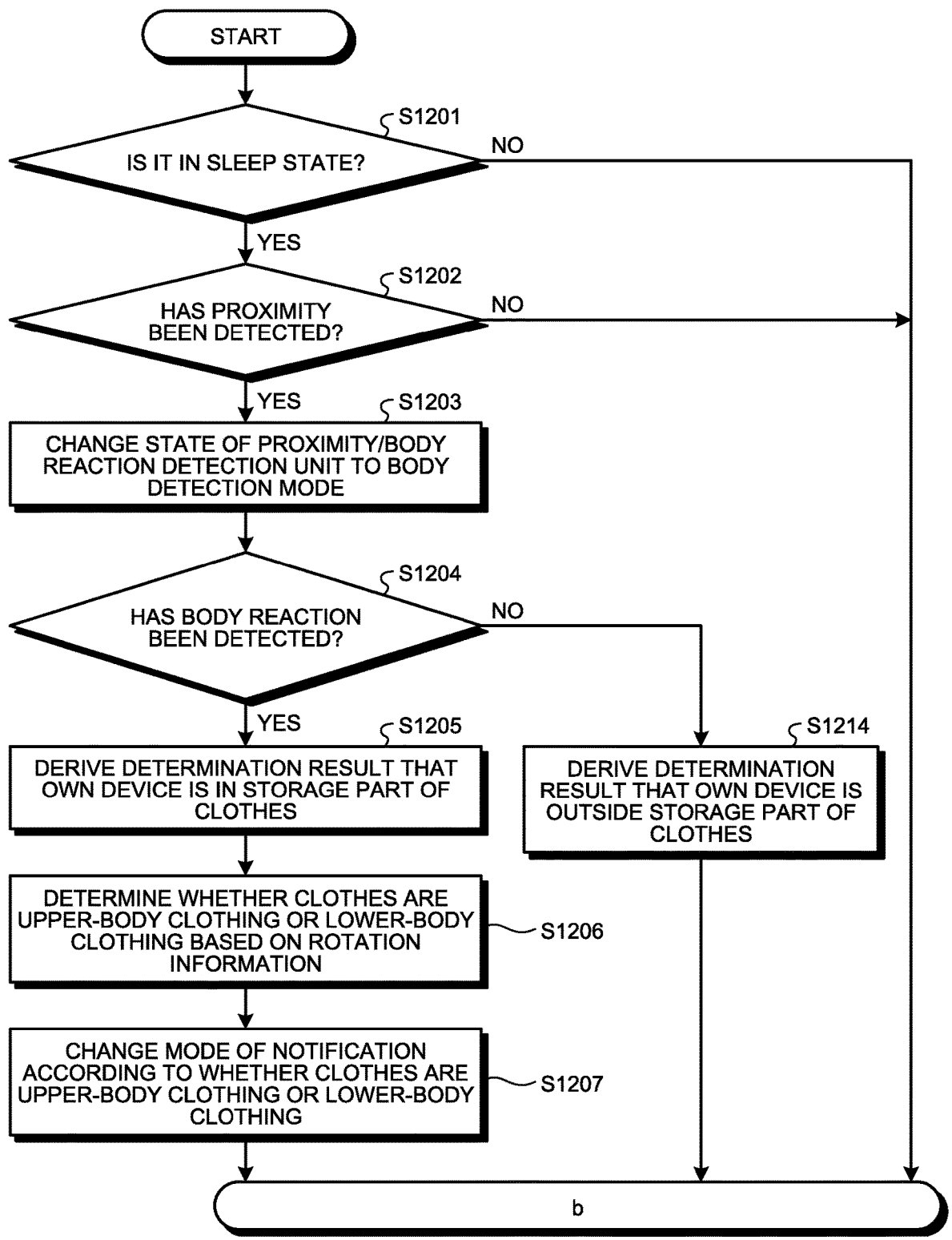
FIG. 15A is a flowchart illustrating an example of the flow of the processing performed by the smartphone.
Figure 15B:
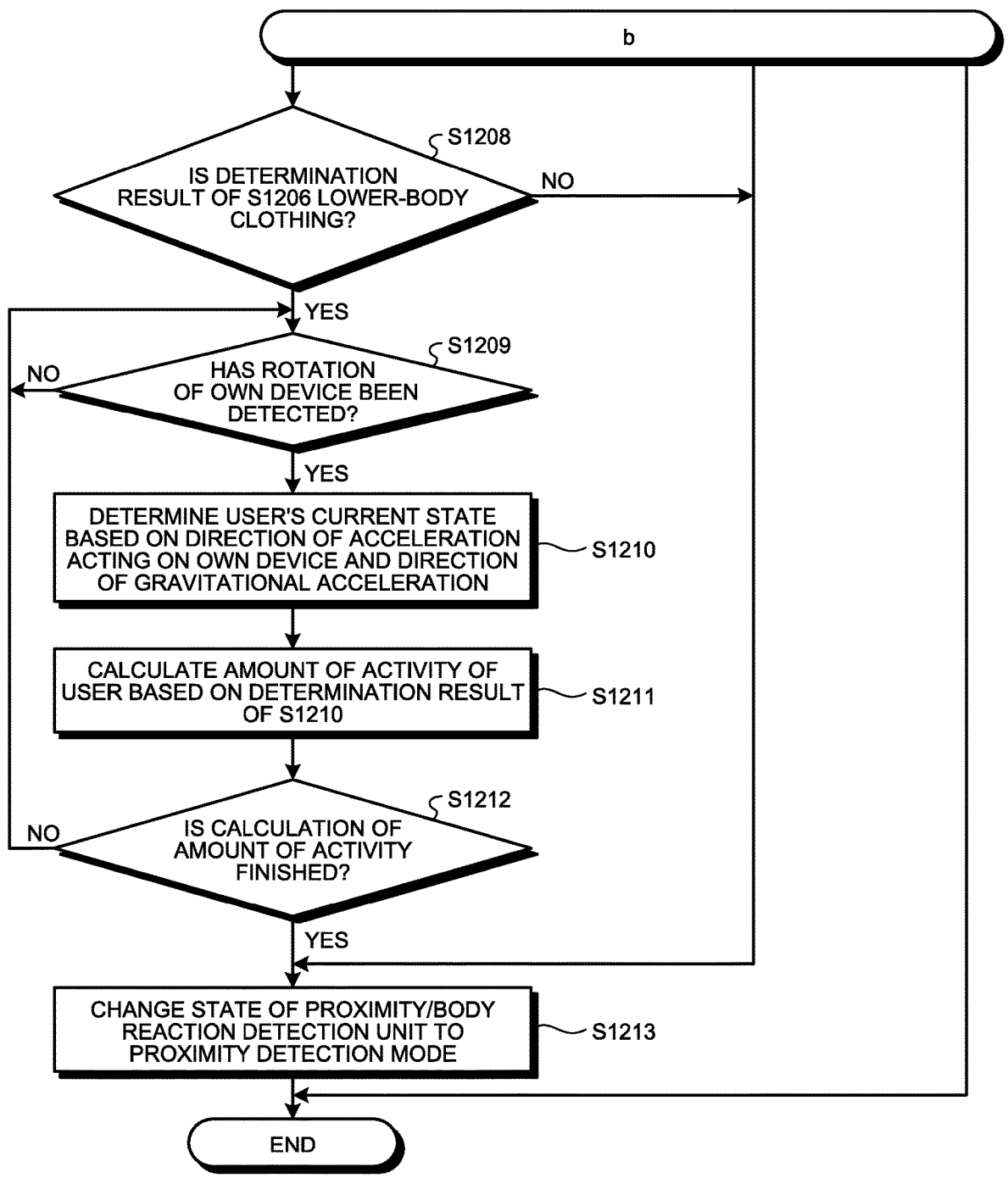
FIG. 15B is a flowchart illustrating an example of the flow of the processing performed by the smartphone.

FIG. 15A and FIG. 15B are flowcharts illustrating an example of the flow of the processing performed by the smartphone 1. The processing illustrated in FIG. 15A and FIG. 15B is implemented by the controller 10 executing the control code 9A or the like stored in the storage 9.

As illustrated in FIG. 15A and FIG. 15B, the controller 10 determines whether the own device is in the sleep state (Step S1201).

When it is determined that the own device is in the sleep state (Yes at Step S1201), the controller 10 determines whether the proximity has been detected (Step S1202).

When it is determined that the proximity has been detected (Yes at Step S1202), the controller 10 changes the operating state of the proximity/body reaction detection unit 17 to the body detection mode (Step S1203).

Subsequently, the controller 10 determines whether the body reaction has been detected (Step S1204).

When it is determined that the body reaction has been detected (Yes at Step S1204), the controller 10 derives a determination result that the own device is in the storage part of the clothes (Step S1205).

The controller 10 then determines whether the clothes are the upper-body clothing or the lower-body clothing based on the rotation information (Step S1206).

Subsequently, the controller 10 changes the mode of notification according to the determination result of Step S1206, i.e., according to whether the clothes are the upper-body clothing or the lower-body clothing (Step S1207).

The controller 10 then determines whether the determination result of Step S1206 is a determination result of "lower-body clothing" (Step S1208).

When the determination result of "lower-body clothing" has been derived by the determination of Step S1206 (Yes at Step S1208), the controller 10 determines whether the rotation of the own device has been detected based on the rotation information (Step S1209). When it is determined that the rotation of the own device has not been detected (No at Step S1209), the controller 10 repeats the determination of Step S1209.

Meanwhile, when it is determined that the rotation of the own device has been detected (Yes at Step S1209), the controller 10 determines the user's current state (standing position or sitting position) based on the direction of acceleration acting on the own device upon detecting the rotation and the direction of gravitational acceleration (Step S1210).

Subsequently, the controller 10 calculates the amount of activity of the user based on the result of determination of Step S1210 (Step S1211).

The controller 10 then determines whether to finish the calculation of the amount of activity (Step S1212). For example, when the sleep state is canceled or when any event such as incoming call occurs, the controller 10 may finish the calculation of the amount of activity.

When it is determined that the calculation of the amount of activity is not finished (No at Step S1212), the controller 10 returns to the procedure of Step S1209. In other words, the smartphone 1 continues the calculation of the amount of activity.

Meanwhile, when it is determined that the calculation of the amount of activity is finished (Yes at Step S1212), the controller 10 changes the operating state of the proximity/body reaction detection unit 17 to the proximity detection mode (Step S1213), and ends the processing illustrated in FIG. 15A and FIG. 15B.

At Step S1208, when the determination result of "lower-body clothing" has not been derived by the determination of Step S1206 (No at Step S1208), the controller 10 proceeds to the procedure of Step S1213.

At Step S1204, when it is determined that the body reaction has not been detected (No at Step S1204), the controller 10 derives a determination result that the own device is outside the storage part of the clothes (Step S1214), and proceeds to the procedure of Step S1213.

At Step S1202, when it is determined that the proximity has not been detected (No at Step S1202), the controller 10 ends the processing illustrated in FIG. 15A and FIG. 15B.

At Step S1201, when it is determined that the own device is not in the sleep state (No at Step S1201), the controller 10 ends the processing illustrated in FIG. 15A and FIG. 15B.

In the embodiments, the smartphone 1 may execute re-notification according to the user's state when there is information to be notified. In the following explanation, the same reference signs may be assigned to the similar components. In the following explanation, overlapping explanation may be omitted. In other words, the smartphone 1 may include the configurations and processing according to the embodiments even if they are not described in the following explanation.

The control code 9A may provide a function for re-notifying the user of the information on condition that there is information to be notified to the user when the user is in the second state as a result of the determination as to whether the user is in the first state in which the user is standing or in the second state in which the user is sitting. The information to be notified includes missed calls, unread incoming mails, schedule notifications, and the like.

When the control code 9A is executed and the user is in the second state as a result of the determination as to whether the user is in the first state in which the user is standing or in the second state in which the user is sitting, the controller 10 can implement the processing for re-notifying the user of information on condition that there is the information to be notified to the user.

Figure 16A:
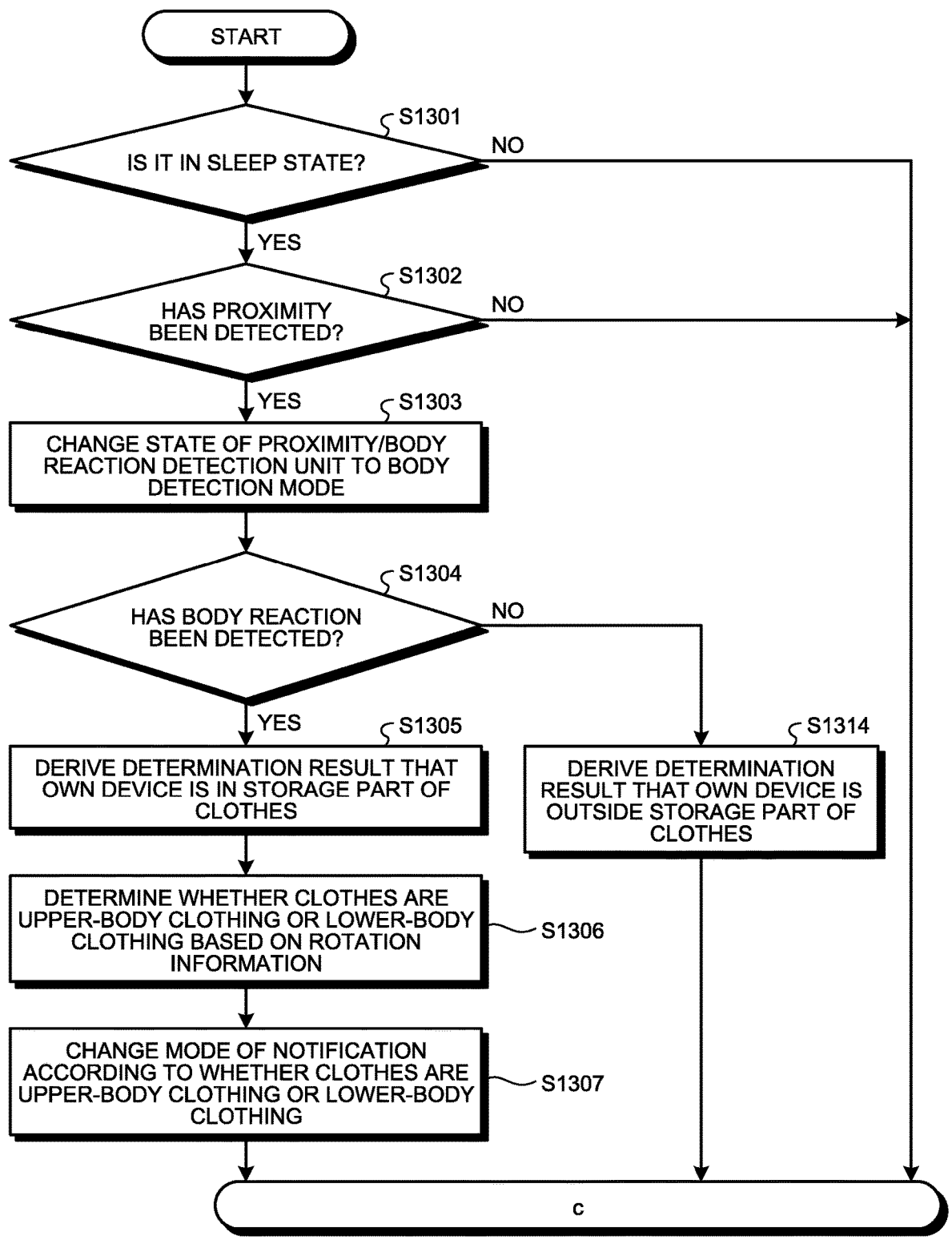
FIG. 16A is a flowchart illustrating an example of the flow of the processing performed by the smartphone.
Figure 16B:
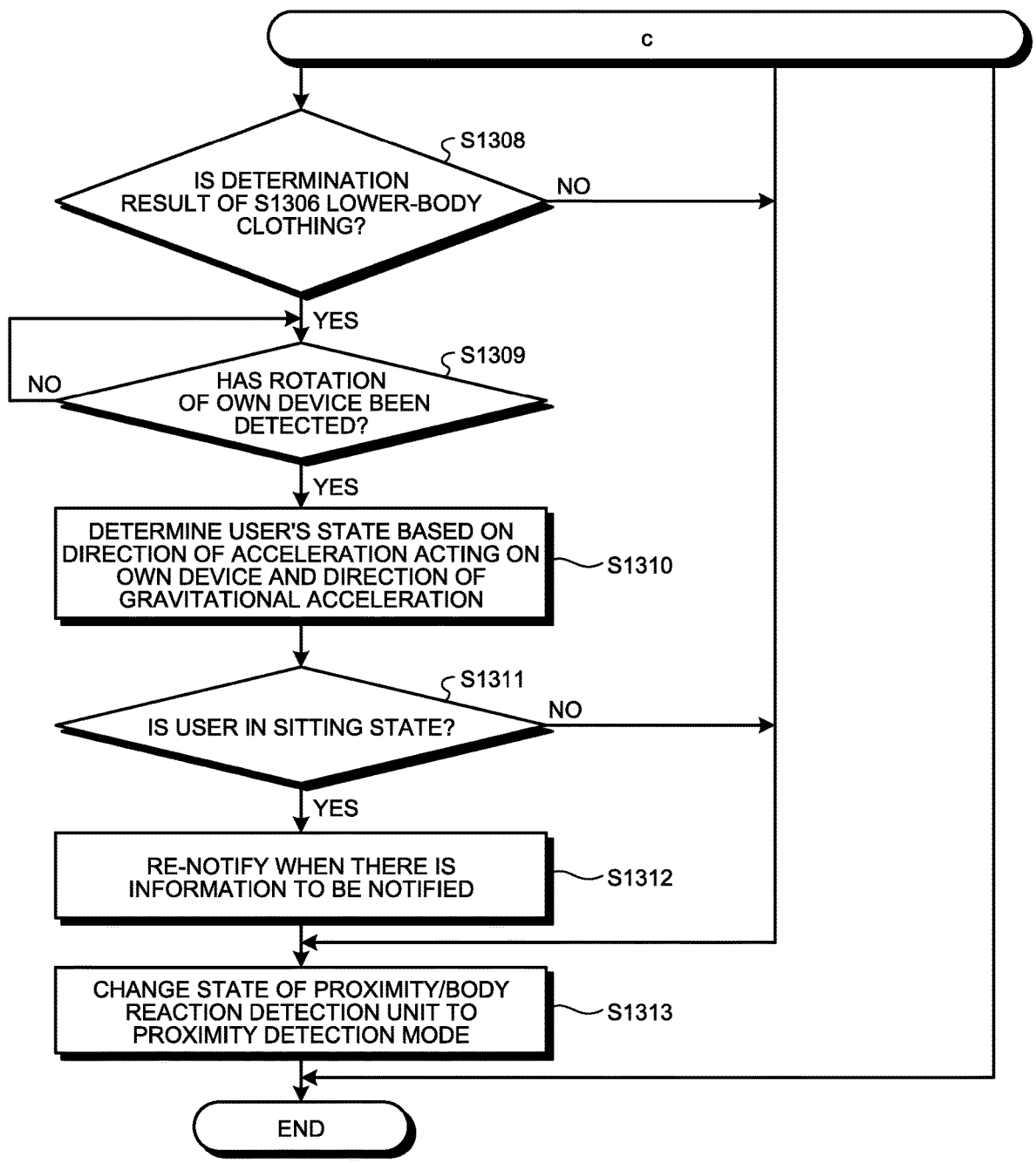
FIG. 16B is a flowchart illustrating an example of the flow of the processing performed by the smartphone.

FIG. 16A and FIG. 16B are flowcharts illustrating an example of the flow of the processing performed by the smartphone 1. The processing illustrated in FIG. 16A and FIG. 16B is implemented by the controller 10 executing the control code 9A or the like stored in the storage 9.

As illustrated in FIG. 16A and FIG. 16B, the controller 10 determines whether the own device is in the sleep state (Step S1301).

When it is determined that the own device is in the sleep state (Yes at Step S1301), the controller 10 determines whether the proximity has been detected (Step S1302).

When it is determined that the proximity has been detected (Yes at Step S1302), the controller 10 changes the operating state of the proximity/body reaction detection unit 17 to the body detection mode (Step S1303).

Subsequently, the controller 10 determines whether the body reaction has been detected (Step S1304).

When it is determined that the body reaction has been detected (Yes at Step S1304), the controller 10 derives a determination result that the own device is in the storage part of the clothes (Step S1305).

The controller 10 then determines whether the clothes are the upper-body clothing or the lower-body clothing based on the rotation information (Step S1306).

Subsequently, the controller 10 changes the mode of notification according to the determination result of Step S1306, i.e., according to whether the clothes are the upper-body clothing or the lower-body clothing (Step S1307).

The controller 10 then determines whether the determination result of Step S1306 is a determination result of "lower-body clothing" (Step S1308).

When the determination result of "lower-body clothing" has been derived by the determination of Step S1306 (Yes at Step S1308), the controller 10 determines whether the rotation of the own device has been detected based on the rotation information (Step S1309). When it is determined that the rotation of the own device has not been detected (No at Step S1309), the controller 10 repeats the determination of Step S1309.

Meanwhile, when it is determined that the rotation of the own device has been detected (Yes at Step S1309), the controller 10 determines the user's current state (standing position or sitting position) based on the direction of acceleration acting on the own device upon detecting the rotation and the direction of gravitational acceleration (Step S1310).

Subsequently, the controller 10 determines whether the determination result of Step S1310 is a determination result of "sitting state (sitting position)" (Step S1311).

When the determination result of "sitting state (sitting position)" has been derived by the determination of Step S1310 (Yes at Step S1311), the controller 10 re-notifies the user of information on condition that there is the information to be notified to the user (Step S1312).

Subsequently, the controller 10 changes the operating state of the proximity/body reaction detection unit 17 to the proximity detection mode (Step S1313), and ends the processing illustrated in FIG. 16A and FIG. 16B.

At Step S1311, when the determination result of "sitting state (sitting position)" has not been derived by the determination of Step S1310 (No at Step S1311), the controller 10 proceeds to the procedure of Step S1313.

At Step S1308, when the determination result of "lower-body clothing" has not been derived (No at Step S1308), the controller 10 proceeds to the procedure of Step S1313.

At Step S1304, when it is determined that the body reaction has not been detected (No at Step S1304), the controller 10 derives a determination result that the own device is outside the storage part of the clothes (Step S1314), and proceeds to the procedure of Step S1313.

At Step S1302, when it is determined that the proximity has not been detected (No at Step S1302), the controller 10 ends the processing illustrated in FIG. 16A and FIG. 16B.

At Step S1301, when it is determined that the own device is not in the sleep state (No at Step S1301), the controller 10 ends the processing illustrated in FIG. 16A and FIG. 16B.

In the embodiments, the smartphone 1 may detect bending and stretching exercises of the user and add the amount of activity of the user caused by the bending and stretching exercises to the amount of activity during calculation. In the following explanation, the same reference signs may be assigned to the similar components. In the following explanation, overlapping explanation may be omitted. In other words, the smartphone 1 may include the configurations and processing according to the embodiments even if they are not described in the following explanation.

The control code 9A can provide a function for determining whether the user has performed the bending and stretching exercises based on the rotation of the own device (smartphone 1) detected based on the rotation information. The control code 9A provides a function for adding a predetermined amount of activity corresponding to the bending and stretching exercises to the amount of activity during calculation. The amount of activity during calculation corresponds to the amount of activity calculated according to the user's state (standing position or sitting position) as explained in the embodiments (see, for example, FIG. 15B). The control code 9A can add a predetermined amount of activity corresponding to the bending and stretching exercises to the amount of activity having been calculated when the bending and stretching exercises are detected. The bending and stretching exercises include a sitting motion from a standing state, a standing motion from a sitting state, going up and down of a lifting facility such as stairs, and repetitive exercises to bend and extend user's legs and the like.

The setting data 9Z include addition data of METs corresponding to the bending and stretching exercises.

The controller 10 executes the control code 9A, and thereby implements the processing of determining whether the user has performed the bending and stretching exercises based on the rotation of the own device (smartphone 1) detected based on the rotation information after the determination that the clothes of the user are the lower-body clothing.

Figure 17A:
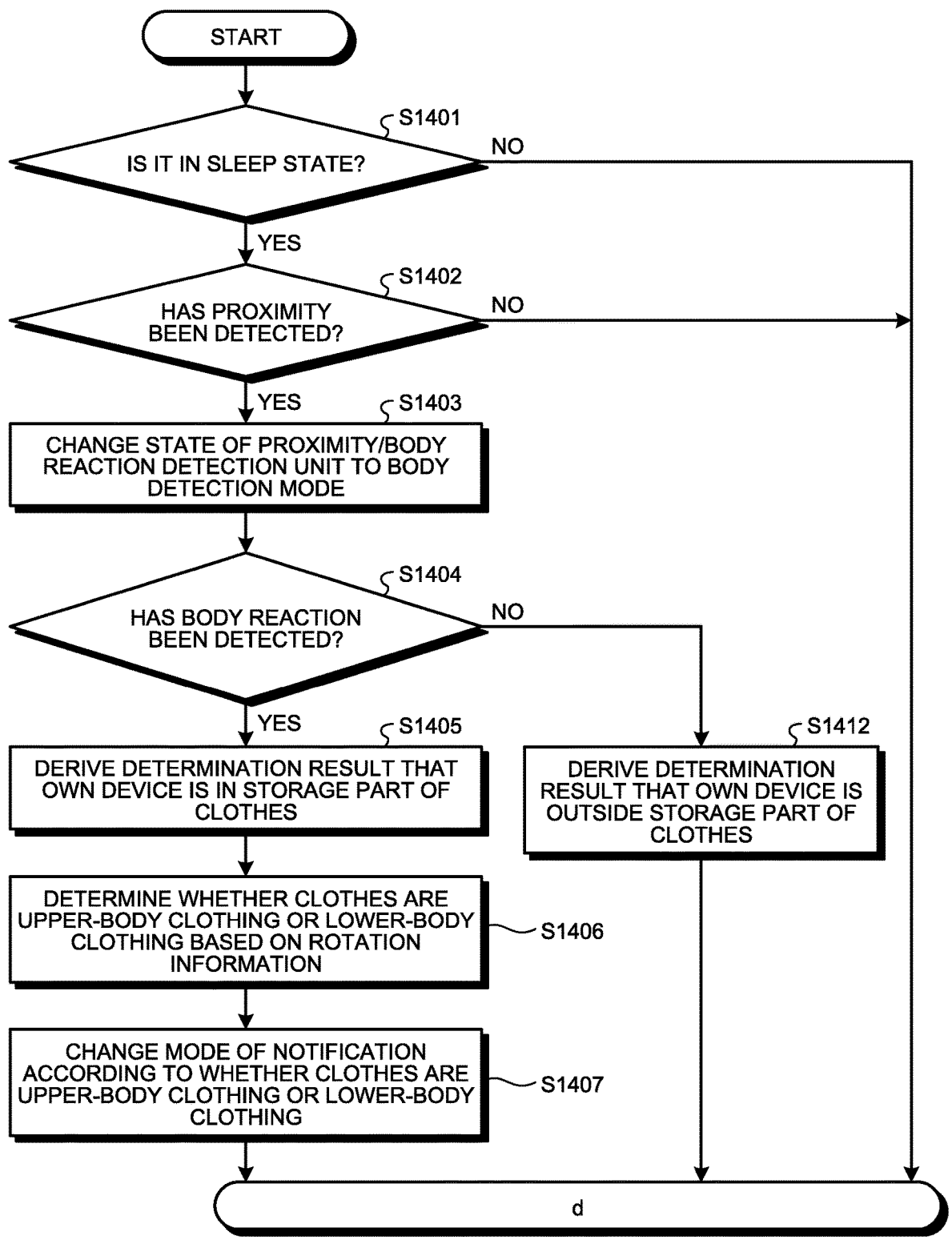
FIG. 17A is a flowchart illustrating an example of the flow of the processing performed by the smartphone.
Figure 17B:
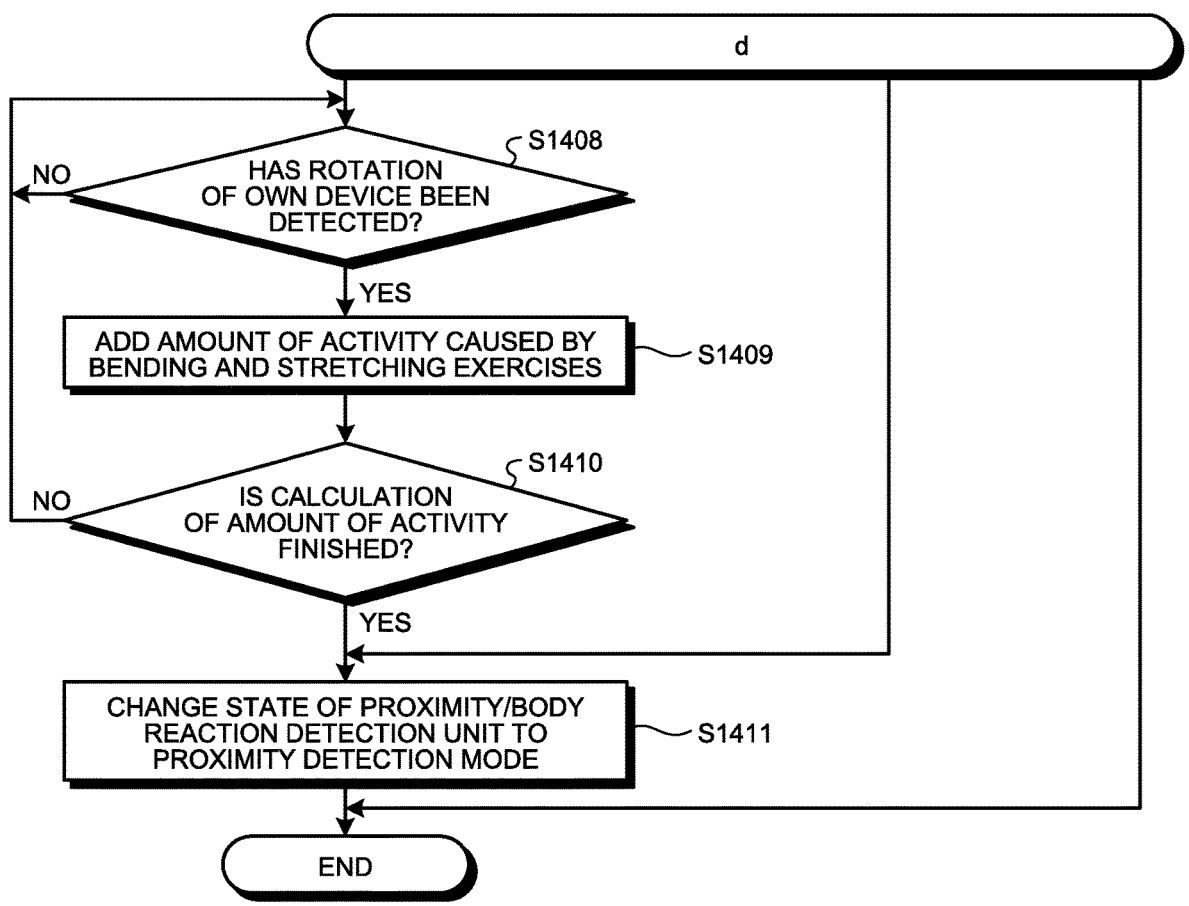
FIG. 17B is a flowchart illustrating an example of the flow of the processing performed by the smartphone.

FIG. 17A and FIG. 17B are flowcharts illustrating an example of the flow of the processing performed by the smartphone 1. The processing illustrated in FIG. 17A and FIG. 17B is implemented by the controller 10 executing the control code 9A or the like stored in the storage 9. The processing according to the embodiments explained below is assumed that the processing (see, for example, FIG. 15B) of calculating the amount of activity according to the user's state is performed in parallel to the processing.

As illustrated in FIG. 17A and FIG. 17B, the controller 10 determines whether the own device is in the sleep state (Step S1401).

When it is determined that the own device is in the sleep state (Yes at Step S1401), the controller 10 determines whether the proximity has been detected (Step S1402).

When it is determined that the proximity has been detected (Yes at Step S1402), the controller 10 changes the operating state of the proximity/body reaction detection unit 17 to the body detection mode (Step S1403).

Subsequently, the controller 10 determines whether the body reaction has been detected (Step S1404).

When it is determined that the body reaction has been detected (Yes at Step S1404), the controller 10 derives a determination result that the own device is in the storage part of the clothes (Step S1405).

The controller 10 then determines whether the clothes are the upper-body clothing or the lower-body clothing based on the rotation information (Step S1406).

Subsequently, the controller 10 changes the mode of notification according to the determination result of Step S1406, i.e., according to whether the clothes are the upper-body clothing or the lower-body clothing (Step S1407).

The controller 10 then determines whether the rotation of the own device has been detected based on the rotation information (Step S1408). When it is determined that the rotation of the own device has not been detected (No at Step S1408), the controller 10 repeats the determination of Step S1408.

When it is determined that the rotation of the own device has been detected (Yes at Step S1408), the controller 10 determines that the user has performed the bending and stretching exercises.

Subsequently, the controller 10 adds a predetermined amount of activity corresponding to the bending and stretching exercises to the amount of activity during calculation (Step S1409). Thus, the controller 10 can add the amount of activity caused by the bending and stretching exercises to the amount of activity calculated according to the user's state each time when user's bending and stretching exercises are detected.

The controller 10 then determines whether the calculation of the amount of activity is finished (Step S1410). For example, when the sleep state is canceled or when any event such as incoming call occurs, the controller 10 may finish the calculation of the amount of activity.

When it is determined that the calculation of the amount of activity is not finished (No at Step S1410), the controller 10 returns to the procedure of Step S1408. In other words, the smartphone 1 continues the detection of the bending and stretching exercises and the addition of a predetermined amount of activity corresponding to the bending and stretching exercises.

Meanwhile, when it is determined that the calculation of the amount of activity is finished (Yes at Step S1410), the controller 10 changes the operating state of the proximity/body reaction detection unit 17 to the proximity detection mode (Step S1411), and ends the processing illustrated in FIG. 17A and FIG. 17B.

At Step S1404, when it is determined that the body reaction has not been detected (No at Step S1404), the controller 10 derives a determination result that the own device is outside the storage part of the clothes (Step S1412), and proceeds to the procedure of Step S1411.

At Step S1402, when it is determined that the proximity has not been detected (No at Step S1402), the controller 10 ends the processing illustrated in FIG. 17A and FIG. 17B.

At Step S1401, when it is determined that the own device is not in the sleep state (No at Step S1401), the controller 10 ends the processing illustrated in FIG. 17A and FIG. 17B.

In the embodiments, when it is determined that the clothes with the storage part in which the own device is stored are the lower-body clothing, the smartphone 1 may stop a communication function based on short-range wireless communications. In the following explanation, the same reference signs may be assigned to the similar components. In the following explanation, overlapping explanation may be omitted. In other words, the smartphone 1 may include the configurations and processing according to the embodiments even if they are not described in the following explanation.

The control code 9A can provide a function for stopping the communication function based on the short-range wireless communications when it is determined that the clothes with the storage part in which the own device (smartphone 1) is stored are the lower-body clothing.

When the control code 9A is executed and it is thereby determined that the clothes with the storage part in which the own device (smartphone 1) is stored are the lower-body clothing, the controller 10 can implement the processing of stopping the communication function based on the short-range wireless communications.

Figure 18:
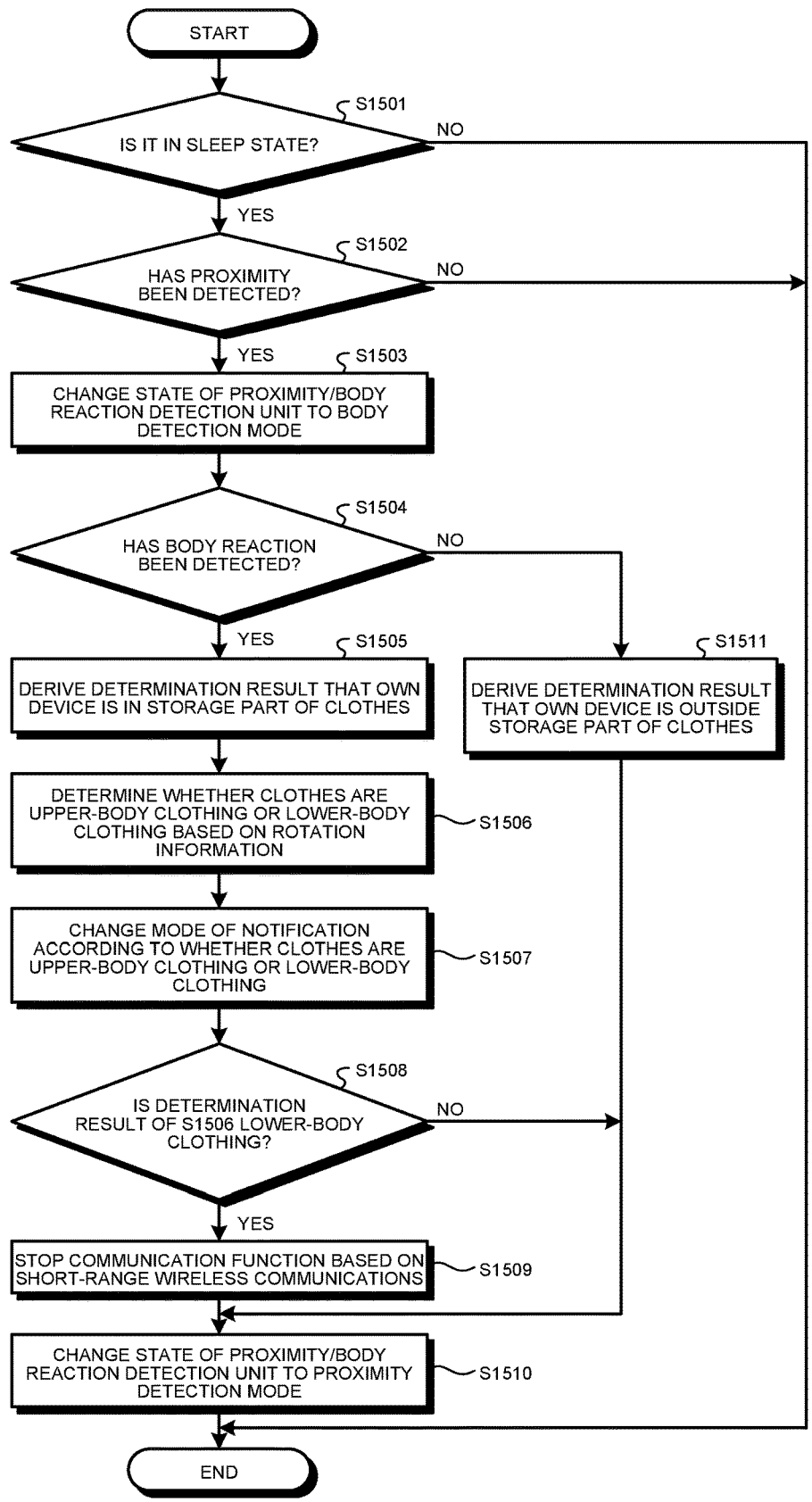
FIG. 18 is a flowchart illustrating an example of the flow of the processing performed by the smartphone.

FIG. 18 is a flowchart illustrating an example of the flow of the processing performed by the smartphone 1. The processing illustrated in FIG. 18 is implemented by the controller 10 executing the control code 9A or the like stored in the storage 9.

As illustrated in FIG. 18, the controller 10 determines whether the own device is in the sleep state (Step S1501).

When it is determined that the own device is in the sleep state (Yes at Step S1501), the controller 10 determines whether the proximity has been detected (Step S1502).

When it is determined that the proximity has been detected (Yes at Step S1502), the controller 10 changes the operating state of the proximity/body reaction detection unit 17 to the body detection mode (Step S1503).

Subsequently, the controller 10 determines whether the body reaction has been detected (Step S1504).

When it is determined that the body reaction has been detected (Yes at Step S1504), the controller 10 derives a determination result that the own device is in the storage part of the clothes (Step S1505).

The controller 10 then determines whether the clothes are the upper-body clothing or the lower-body clothing based on the rotation information (Step S1506).

Subsequently, the controller 10 changes the mode of notification according to the determination result of Step S1506, i.e., according to whether the clothes are the upper-body clothing or the lower-body clothing (Step S1507).

The controller 10 then determines whether the determination result of Step S1506 is a determination result of "lower-body clothing" (Step S1508).

Subsequently, when the determination result of "lower-body clothing" has been derived by the determination of Step S1506 (Yes at Step S1508), the controller 10 stops the communication function based on the short-range wireless communications (Step S1509).

The controller 10 then changes the operating state of the proximity/body reaction detection unit 17 to the proximity detection mode (Step S1510), and ends the processing illustrated in FIG. 18.

At Step S1508, when the determination result of "lower-body clothing" has not been derived by the determination of Step S1506 (No at Step S1508), the controller 10 proceeds to the procedure of Step S1510.

At Step S1504, when it is determined that the body reaction has not been detected (No at Step S1504), the controller 10 derives a determination result that the own device is outside the storage part of the clothes (Step S1511), and proceeds to the procedure of Step S1510.

At Step S1502, when it is determined that the proximity has not been detected (No at Step S1502), the controller 10 ends the processing illustrated in FIG. 18.

At Step S1501, when it is determined that the own device is not in the sleep state (No at Step S1501), the controller 10 ends the processing illustrated in FIG. 18.

In the embodiments, the smartphone 1 has been explained as an example of the device, however, the embodiments are not limited to the smartphone 1. The device may be any device other than the smartphone if the device is an electronic device that can be stored in the storage part of clothes.

Although the art of appended claims has been described with respect to specific embodiments for a complete and clear disclosure, the appended claims are not to be thus limited but are to be construed as embodying all modifications and alternative constructions that may occur to one skilled in the art which fairly fall within the basic teaching herein set forth.

In the present application, the descriptions such as "when", "during", "if", "in a case", "upon", "in response to determining", and "in response to detecting" may be understood in place of other descriptions depending on situations. In the present application, the descriptions such as "when 'a stated condition or event' is determined", "when 'a stated condition or event' is detected", or "upon determining 'a stated condition or event'", "in response to determining", "upon detecting", or "in response to detecting" may be understood in place of other descriptions depending on situations. In the present application, the description such as "detect" may be understood as meaning of "measure", "scale", and "sense" depending on situations. In the present application, the description such as "state" may be understood as "situation" depending on situations. For example, the moving state can be understood as "moving situation". The state of the mobile electronic phone can be understood as "situation of the mobile electronic device".

The invention claimed is:
1. A mobile electronic device, comprising:
a first sensor configured to detect a proximity to the mobile electronic device;
a second sensor configured to detect a body reaction including at least one of a heart rate of a user of the mobile electronic device, heart beats of the user, or an electrical signal generated by the heart of the user; and a controller configured to determine, when the proximity to the mobile electronic device is detected by the first sensor and the body reaction is detected by the second sensor, that the mobile electronic device is in a storage part provided on clothes, wherein,
when it is determined that the mobile electronic device is in the storage part provided on the clothes, the controller is configured to determine whether the clothes correspond to upper-body clothing or lower-body clothing of the user based on rotation information of the mobile electronic device while the mobile electronic device remains stored in the storage part provided on the clothes, the determination whether the clothes correspond to the upper-body clothing or the lower-body clothing of the user is performed in response to at least one of
(i) the mobile electronic device being in a sleep state, or
(ii) a transition of the mobile electronic device from an active state to the sleep state, and the determination whether the clothes correspond to the upper-body clothing or the lower-body clothing of the user is not performed while the mobile electronic device is being in the active state.

2. The mobile electronic device according to claim 1, wherein, when the proximity to the mobile electronic device is detected by the first sensor and the body reaction is not detected by the second sensor,
the controller is configured to determine that the mobile electronic device is outside the storage part.

3. The mobile electronic device according to claim 1, wherein
the controller is configured to determine that the mobile electronic device is in the storage part on condition that the proximity to the mobile electronic device is continuously detected by the first sensor after it is determined that the mobile electronic device is in the storage part.

4. The mobile electronic device according to claim 1, wherein
the controller is configured to determine that the mobile electronic device is in the storage part on condition that the body reaction is continuously detected by the second sensor after it is determined that the mobile electronic device is in the storage part.

5. The mobile electronic device according to claim 1, wherein, when the mobile electronic device is in the sleep state,
the controller is configured to perform determination as to whether the mobile electronic device is in the storage part.

6. The mobile electronic device according to claim 1, wherein
the controller is configured to perform determination as to whether the mobile electronic device is in the storage part on condition that the mobile electronic device transitions from the active state to the sleep state.

7. The mobile electronic device according to claim 1, further comprising:
a third sensor configured to detect a change of a moving state of the mobile electronic device, wherein
the controller is configured to perform determination as to whether the mobile electronic device is in the storage part on condition that the third sensor detects the change of the moving state of the mobile electronic device.

8. The mobile electronic device according to claim 1, wherein
the controller is configured to perform determination as to whether the mobile electronic device is in the storage part on condition that an event occurs.

9. The mobile electronic device according to claim 1, wherein the second sensor is an acceleration sensor configured to detect the heart beats of the user.

10. A mobile electronic device comprising:
a sensor configured to detect a proximity to the mobile electronic device and a body reaction triggered by detection of the proximity to the mobile electronic device;
a gyroscope configured to detect information on a rotation of the mobile electronic device; and
a controller configured to determine, when the body reaction is detected by the sensor, that the mobile electronic device is in a storage part provided on clothes, wherein
the controller is configured to determine whether the clothes correspond to upper-body clothing or lower-body clothing of a user based on the information on the rotation acquired after it is determined that the mobile electronic device is in the storage part, in response to a determination that the clothes correspond to the lower-body clothing, the controller is configured to determine, based on a direction of acceleration acting on the mobile device when the rotation is detected and a direction of gravitational acceleration, whether the user is in a first state in which the user is standing or in a second state in which the user is sitting and the sensor is an acceleration sensor configured to detect heart beats of the user, the determination whether the clothes correspond to the upper-body clothing or the lower-body clothing of the user is performed in response to at least one of
(i) the mobile electronic device being in a sleep state, or
(ii) a transition of the mobile electronic device from an active state to the sleep state, and the determination whether the clothes correspond to the upper-body clothing or the lower-body clothing of the user is not performed while the mobile electronic device is being in the active state.

11. The mobile electronic device according to claim 10, wherein
the controller is configured to change a mode of notification to the user depending on a case where it is determined that the clothes are the upper-body clothing or a case where it is determined that the clothes are the lower-body clothing as a result of the determination whether the clothes correspond to the upper-body clothing or the lower-body clothing of the user.

12. The mobile electronic device according to claim 11, wherein
the controller is configured to make greater an output intensity of notification by vibration executed when the clothes are determined as the upper-body clothing than an output intensity of notification by vibration executed when the clothes are determined as the lower-body clothing.

13. The mobile electronic device according to claim 11, wherein
the controller is configured to make longer an output time of notification by vibration executed when the clothes are determined as the upper-body clothing than an output time of notification by vibration executed when the clothes are determined as the lower-body clothing.

14. The mobile electronic device according to claim 10, wherein the controller is configured to derive a determination result that the state of the user before the determination is the second state when it is determined that the user is in the first state, and derive a determination result that the state of the user before the determination is the first state when it is determined that the user is in the second state.

15. The mobile electronic device according to claim 10, wherein the controller is configured to calculate the amount of activity of the user based on a determination result as to whether the user is in the first state or in the second state.

16. The mobile electronic device according to claim 10, wherein the controller is configured to re-notify the user of information on condition that there is the information to be notified to the user in response to determining the user being in the second state, and the information to be notified is at least one of missed calls, unread incoming mails, or schedule notification.

17. The mobile electronic device according to claim 10, further comprising another sensor configured to detect bending and stretching exercises of the user based on the rotation information, wherein the controller is configured to cause the another sensor to detect the bending and stretching exercises of the user based on the rotation information after it is determined that the clothes are the lower-body clothing.

18. The mobile electronic device according to claim 10, wherein the controller is configured to stop communication based on short-range wireless communications when it is determined that the clothes are the lower-body clothing.

19. A mobile electronic device, comprising:

a first sensor configured to detect a proximity to the mobile electronic device;

a second sensor configured to detect a body reaction including at least one of a heart rate of a user of the mobile electronic device, heart beats of the user, or an electrical signal generated by the heart of the user; and a controller configured to perform determination as to whether the mobile electronic device is in a storage part provided on clothes, triggered by at least one of (i) the mobile electronic device being in a sleep state, or (ii) a transition of the mobile electronic device from an active state to the sleep state, and not perform the determination as to whether the mobile electronic device is in a storage part provided on clothes while the mobile electronic device is being in the active state, wherein the controller is configured to determine, when the proximity to the mobile electronic device is detected by the first sensor and the body reaction is detected by the second sensor, that the mobile electronic device is in the storage part provided on the clothes, and when it is determined that the mobile electronic device is in the storage part provided on the clothes, the controller is configured to determine whether the clothes correspond to upper-body clothing or lower-body clothing of the user based on rotation information of the mobile electronic device.

* * * * *